United States Patent
Yadav

(10) Patent No.: US 10,575,968 B2
(45) Date of Patent: Mar. 3, 2020

(54) GUIDES FOR FRACTURE SYSTEM

(71) Applicant: Howmedica Osteonics Corp., Mahwah, NJ (US)

(72) Inventor: Rajan Yadav, New Delhi (IN)

(73) Assignee: Howmedica Osteonics Corp., Mahwah, NJ (US)

( * ) Notice: Subject to any disclaimer, the term of this patent is extended or adjusted under 35 U.S.C. 154(b) by 368 days.

(21) Appl. No.: 15/601,100

(22) Filed: May 22, 2017

(65) Prior Publication Data

US 2017/0258607 A1    Sep. 14, 2017

Related U.S. Application Data

(63) Continuation-in-part of application No. 14/279,572, filed on May 16, 2014, now Pat. No. 9,681,960.

(51) Int. Cl.
| | |
|---|---|
| *A61F 2/46* | (2006.01) |
| *A61F 2/40* | (2006.01) |
| *A61F 2/32* | (2006.01) |
| *G01B 5/06* | (2006.01) |

(Continued)

(52) U.S. Cl.
CPC .............. *A61F 2/4657* (2013.01); *A61F 2/32* (2013.01); *A61F 2/4014* (2013.01); *A61F 2/4059* (2013.01); *A61F 2/4612* (2013.01); *A61F 2/4684* (2013.01); *G01B 3/20* (2013.01); *G01B 5/065* (2013.01); *A61F 2002/30492* (2013.01); *A61F 2002/30507* (2013.01); *A61F 2002/30579* (2013.01); *A61F 2002/30617* (2013.01); *A61F 2002/30649* (2013.01); *A61F 2002/4051* (2013.01); *A61F 2002/4658* (2013.01);

(Continued)

(58) Field of Classification Search
CPC .............. A61F 2/40–2002/4096; A61F 2/4657
See application file for complete search history.

(56) References Cited

U.S. PATENT DOCUMENTS

| | | |
|---|---|---|
| 1,659,915 A | 2/1928 | Hilfiker |
| 2,304,265 A | 12/1942 | Magyari |
| 2,783,541 A | 3/1957 | Naab |

(Continued)

OTHER PUBLICATIONS

Zimmer, Anatomical Shoulder Fracture System Surgical Technique, 2010, pp. 1-24.

(Continued)

*Primary Examiner* — Zade Coley
(74) *Attorney, Agent, or Firm* — Lerner, David, Littenberg, Krumholz & Mentlik, LLP

(57) ABSTRACT

A prosthetic shoulder implant system includes a prosthetic humeral implant and a version device. The humeral implant includes a catch member aperture and a first locking pin aperture. The version device includes a rotatable member with a body and a flexure member, and a plate with a catch member and a projection contacting the flexure member. A first locking pin extends from the version device and is adapted to mate with the first locking pin aperture. In an unlocked condition of the system, the rotatable member has a first rotated position in which the flexure member is in an uncompressed state and the plate is in a first position, and in a locked condition of the system, the rotatable member has a second rotated position in which the flexure member is in a compressed state and the plate is in a second position proximal of the first position.

20 Claims, 16 Drawing Sheets

(51) Int. Cl.
*G01B 3/20* (2006.01)
*A61F 2/30* (2006.01)
(52) U.S. Cl.
CPC ............... *A61F 2002/4662* (2013.01); *A61F 2002/4668* (2013.01); *A61F 2002/4687* (2013.01)

(56) References Cited

U.S. PATENT DOCUMENTS

| | | | |
|---|---|---|---|
| 3,102,536 A | 9/1963 | Rose | |
| 4,266,302 A | 5/1981 | Tornier | |
| 4,287,617 A | 9/1981 | Tornier | |
| 4,483,335 A | 11/1984 | Tornier | |
| 4,488,543 A | 12/1984 | Tornier | |
| 4,583,270 A * | 4/1986 | Kenna | A61B 17/1659 30/169 |
| 5,147,408 A * | 9/1992 | Noble | A61F 2/30724 606/85 |
| 5,171,289 A | 12/1992 | Tornier | |
| 5,190,550 A * | 3/1993 | Miller | A61B 17/1659 606/85 |
| 5,314,485 A | 5/1994 | Judet | |
| 5,324,293 A * | 6/1994 | Rehmann | A61B 17/1659 606/85 |
| 5,326,359 A | 7/1994 | Oudard | |
| 5,358,526 A | 10/1994 | Tornier | |
| 5,405,399 A | 4/1995 | Tornier | |
| 5,429,639 A | 7/1995 | Judet | |
| 5,443,471 A * | 8/1995 | Swajger | A61B 17/1659 403/294 |
| 5,458,650 A | 10/1995 | Carret et al. | |
| 5,505,731 A | 4/1996 | Tornier | |
| 5,562,672 A | 10/1996 | Huebner et al. | |
| 5,591,168 A | 1/1997 | Judet et al. | |
| 5,616,147 A | 4/1997 | Gadelius | |
| 5,624,440 A | 4/1997 | Huebner | |
| 5,658,283 A | 8/1997 | Huebner | |
| 5,662,649 A | 9/1997 | Huebner | |
| 5,662,651 A | 9/1997 | Tornier et al. | |
| 5,665,087 A | 9/1997 | Huebner | |
| 5,676,702 A | 10/1997 | Ratron | |
| 5,697,934 A | 12/1997 | Huebner | |
| 5,700,268 A | 12/1997 | Bertin | |
| 5,702,447 A | 12/1997 | Walch et al. | |
| 5,702,457 A | 12/1997 | Walch et al. | |
| 5,702,472 A | 12/1997 | Huebner | |
| 5,702,478 A | 12/1997 | Tornier | |
| 5,766,256 A | 6/1998 | Oudard et al. | |
| 5,776,194 A | 7/1998 | Mikol et al. | |
| 5,792,143 A | 8/1998 | Samuelson et al. | |
| 5,800,551 A | 9/1998 | Williamson et al. | |
| 5,810,825 A | 9/1998 | Huebner | |
| 5,824,106 A | 10/1998 | Fournol | |
| 5,868,789 A | 2/1999 | Huebner | |
| 5,871,486 A | 2/1999 | Huebner et al. | |
| 5,879,395 A | 3/1999 | Tornier et al. | |
| 5,928,285 A | 7/1999 | Bigliani et al. | |
| 5,944,721 A | 8/1999 | Huebner | |
| 5,944,758 A | 8/1999 | Mansat et al. | |
| 5,961,555 A | 10/1999 | Huebner | |
| 5,964,768 A | 10/1999 | Huebner | |
| 5,976,134 A | 11/1999 | Huebner | |
| 6,001,099 A | 12/1999 | Huebner | |
| 6,015,437 A | 1/2000 | Stossel | |
| 6,017,347 A | 1/2000 | Huebner et al. | |
| 6,022,377 A | 2/2000 | Nuelle et al. | |
| 6,030,162 A | 2/2000 | Huebner | |
| 6,056,756 A | 5/2000 | Eng et al. | |
| 6,077,271 A | 6/2000 | Huebner et al. | |
| 6,102,953 A | 8/2000 | Huebner | |
| 6,106,529 A | 8/2000 | Techiera | |
| 6,113,605 A * | 9/2000 | Storer | A61F 2/4607 606/86 R |
| 6,120,505 A | 9/2000 | Huebner | |
| 6,120,507 A | 9/2000 | Allard et al. | |
| 6,162,224 A | 12/2000 | Huebner | |
| 6,162,254 A | 12/2000 | Timoteo | |
| 6,165,224 A | 12/2000 | Tornier | |
| 6,168,627 B1 | 1/2001 | Huebner | |
| 6,168,628 B1 | 1/2001 | Huebner | |
| 6,168,629 B1 | 1/2001 | Timoteo | |
| 6,171,309 B1 | 1/2001 | Huebner | |
| 6,171,341 B1 | 1/2001 | Boileau et al. | |
| 6,183,519 B1 | 2/2001 | Bonnin et al. | |
| 6,193,758 B1 | 2/2001 | Huebner | |
| 6,197,063 B1 | 3/2001 | Dews | |
| 6,205,884 B1 * | 3/2001 | Foley | A61B 17/1659 606/85 |
| 6,206,884 B1 | 3/2001 | Masini | |
| 6,206,925 B1 | 3/2001 | Tornier | |
| 6,228,119 B1 | 5/2001 | Ondrla et al. | |
| 6,228,120 B1 | 5/2001 | Leonard et al. | |
| 6,245,074 B1 | 6/2001 | Allard et al. | |
| 6,277,123 B1 | 8/2001 | Maroney et al. | |
| 6,283,999 B1 | 9/2001 | Rockwood, Jr. | |
| 6,299,615 B1 | 10/2001 | Huebner | |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,364,910 B1 | 4/2002 | Shultz et al. | |
| 6,368,352 B1 | 4/2002 | Camino et al. | |
| 6,368,353 B1 | 4/2002 | Arcand | |
| 6,379,387 B1 | 4/2002 | Tornier | |
| 6,454,809 B1 | 9/2002 | Tornier | |
| 6,458,136 B1 | 10/2002 | Allard et al. | |
| 6,488,712 B1 | 12/2002 | Tornier et al. | |
| 6,494,913 B1 | 12/2002 | Huebner | |
| 6,508,840 B1 | 1/2003 | Rockwood, Jr. et al. | |
| 6,530,957 B1 | 3/2003 | Jack | |
| 6,540,770 B1 | 4/2003 | Tornier et al. | |
| 6,554,865 B2 | 4/2003 | Grusin et al. | |
| 6,558,425 B2 | 5/2003 | Rockwood, Jr. | |
| 6,582,469 B1 | 6/2003 | Tornier | |
| 6,589,281 B2 | 7/2003 | Hyde, Jr. | |
| 6,589,282 B2 | 7/2003 | Pearl | |
| 6,599,295 B1 | 7/2003 | Tornier et al. | |
| 6,620,197 B2 | 9/2003 | Maroney et al. | |
| 6,626,913 B1 * | 9/2003 | McKinnon | A61F 2/367 606/86 R |
| 6,626,946 B1 | 9/2003 | Walch et al. | |
| 6,676,705 B1 | 1/2004 | Wolf | |
| 6,679,916 B1 | 1/2004 | Frankle et al. | |
| 6,699,289 B2 | 3/2004 | Iannotti et al. | |
| 6,730,094 B2 | 5/2004 | Salyer et al. | |
| 6,736,851 B2 | 5/2004 | Maroney et al. | |
| 6,736,852 B2 | 5/2004 | Callaway et al. | |
| 6,749,637 B1 | 6/2004 | Bahler | |
| 6,761,740 B2 | 7/2004 | Tornier | |
| 6,767,368 B2 | 7/2004 | Tornier | |
| 6,783,549 B1 | 8/2004 | Stone et al. | |
| 6,790,234 B1 | 9/2004 | Frankle | |
| 6,818,019 B2 | 11/2004 | Horber | |
| 6,824,567 B2 | 11/2004 | Tornier et al. | |
| 6,863,690 B2 | 3/2005 | Ball et al. | |
| 6,890,357 B2 | 5/2005 | Tornier | |
| 6,908,486 B2 | 6/2005 | Lewallen | |
| 6,911,047 B2 | 6/2005 | Rockwood, Jr. et al. | |
| 6,942,699 B2 | 9/2005 | Stone et al. | |
| 6,951,563 B2 | 10/2005 | Wolford | |
| 6,953,478 B2 | 10/2005 | Bouttens et al. | |
| 6,969,406 B2 | 11/2005 | Tornier | |
| 6,984,235 B2 | 1/2006 | Huebner | |
| 7,011,686 B2 | 3/2006 | Ball et al. | |
| 7,033,396 B2 | 4/2006 | Tornier | |
| 7,044,976 B2 | 5/2006 | Meswania | |
| 7,160,328 B2 | 1/2007 | Rockwood, Jr. et al. | |
| 7,169,184 B2 | 1/2007 | Dalla Pria | |
| 7,175,663 B1 | 2/2007 | Stone | |
| 7,189,261 B2 | 3/2007 | Dews et al. | |
| 7,217,272 B2 | 5/2007 | Salyer | |
| 7,238,207 B2 | 7/2007 | Blatter et al. | |
| 7,241,314 B1 | 7/2007 | Winslow | |
| 7,294,133 B2 | 11/2007 | Zink et al. | |

(56) References Cited

U.S. PATENT DOCUMENTS

| | | |
|---|---|---|
| 7,297,163 B2 | 11/2007 | Huebner |
| 7,303,585 B2 | 12/2007 | Horber |
| 7,309,360 B2 | 12/2007 | Tornier et al. |
| 7,329,284 B2 | 2/2008 | Maroney et al. |
| 7,335,204 B2 | 2/2008 | Tornier |
| 7,338,496 B1 | 3/2008 | Winslow et al. |
| 7,338,498 B2 | 3/2008 | Long et al. |
| 7,338,528 B2 | 3/2008 | Stone et al. |
| 7,364,694 B2 | 4/2008 | Tornier |
| 7,396,357 B2 | 7/2008 | Tornier et al. |
| 7,431,736 B2 | 10/2008 | Maroney et al. |
| 7,435,263 B2 | 10/2008 | Barnett et al. |
| 7,445,638 B2 | 11/2008 | Beguin et al. |
| 7,462,197 B2 | 12/2008 | Tornier et al. |
| 7,465,319 B2 | 12/2008 | Tornier |
| 7,468,077 B2 | 12/2008 | Rochetin |
| 7,470,287 B2 | 12/2008 | Tornier et al. |
| 7,476,227 B2 | 1/2009 | Tornier et al. |
| 7,503,921 B2 | 3/2009 | Berthusen et al. |
| 7,517,364 B2 | 4/2009 | Long et al. |
| 7,544,211 B2 | 6/2009 | Rochetin |
| 7,556,652 B2 | 7/2009 | Angibaud et al. |
| 7,588,572 B2 | 9/2009 | White et al. |
| 7,604,665 B2 | 10/2009 | Iannotti et al. |
| 7,608,075 B2 | 10/2009 | Tornier |
| 7,621,915 B2 | 11/2009 | Frederick et al. |
| 7,678,150 B2 | 3/2010 | Tornier et al. |
| 7,699,853 B2 | 4/2010 | Durand-Allen et al. |
| 7,735,237 B1 | 6/2010 | Moon |
| 7,753,959 B2 | 7/2010 | Berelsman et al. |
| 7,758,614 B2 | 7/2010 | Fenton et al. |
| 7,854,768 B2 | 12/2010 | Wiley et al. |
| 7,879,105 B2 | 2/2011 | Schmieding et al. |
| 7,879,275 B2 | 2/2011 | Smith et al. |
| 7,883,653 B2 | 2/2011 | Smith et al. |
| 7,887,544 B2 | 2/2011 | Tornier et al. |
| 7,892,287 B2 | 2/2011 | Deffenbaugh |
| 7,896,921 B2 | 3/2011 | Smith et al. |
| 7,918,856 B2 | 4/2011 | Guelat et al. |
| 7,918,892 B2 | 4/2011 | Huebner |
| 7,922,728 B2 | 4/2011 | Tornier et al. |
| 7,922,769 B2 | 4/2011 | Deffenbaugh et al. |
| 7,927,335 B2 | 4/2011 | Deffenbaugh et al. |
| 7,927,338 B2 | 4/2011 | Laffargue et al. |
| 7,938,847 B2 | 5/2011 | Fanton et al. |
| 7,942,882 B2 | 5/2011 | Tornier et al. |
| 7,951,204 B2 | 5/2011 | Chambat et al. |
| 7,959,680 B2 | 6/2011 | Stone et al. |
| 7,981,161 B2 | 7/2011 | Choi et al. |
| 7,993,346 B2 | 8/2011 | Tornier et al. |
| 8,002,839 B2 | 8/2011 | Rochetin et al. |
| 8,007,538 B2 | 8/2011 | Gunther |
| 8,014,984 B2 | 9/2011 | Iannotti et al. |
| 8,016,836 B2 | 9/2011 | Corrao et al. |
| RE42,805 E | 10/2011 | Tornier et al. |
| 8,029,536 B2 | 10/2011 | Sorensen et al. |
| D648,027 S | 11/2011 | Vancelette et al. |
| 8,048,161 B2 | 11/2011 | Guederian et al. |
| 8,062,376 B2 | 11/2011 | Shultz et al. |
| 8,070,786 B2 | 12/2011 | Huebner et al. |
| 8,070,820 B2 | 12/2011 | Winslow et al. |
| 8,075,563 B2 | 12/2011 | Guelat et al. |
| 8,080,063 B2 | 12/2011 | Ferrand et al. |
| 8,088,168 B2 | 1/2012 | Hassler et al. |
| 8,092,547 B2 | 1/2012 | Lepow et al. |
| 8,105,327 B2 | 1/2012 | Long et al. |
| 8,109,942 B2 | 2/2012 | Carson |
| 8,114,091 B2 | 2/2012 | Ratron et al. |
| 8,118,849 B2 | 2/2012 | Wahl et al. |
| 8,118,875 B2 | 2/2012 | Rollet |
| 8,123,753 B2 | 2/2012 | Poncet |
| 8,137,359 B2 | 3/2012 | Poncet |
| 8,147,531 B2 | 4/2012 | Corrao et al. |
| 8,157,866 B2 | 4/2012 | Winslow et al. |
| 8,182,541 B2 | 5/2012 | Long et al. |
| 8,187,282 B2 | 5/2012 | Tornier et al. |
| 8,192,453 B2 | 6/2012 | Valla |
| 8,197,487 B2 | 6/2012 | Poncet et al. |
| 8,197,492 B2 | 6/2012 | Poncet |
| 8,197,508 B2 | 6/2012 | Egan et al. |
| 8,216,320 B2 | 7/2012 | Splieth et al. |
| 8,231,682 B2 | 7/2012 | Lafosse et al. |
| 8,231,683 B2 | 7/2012 | Lappin et al. |
| 8,231,684 B2 | 7/2012 | Mutchler et al. |
| 8,235,995 B2 | 8/2012 | Focht et al. |
| 8,241,289 B2 | 8/2012 | Maisonneuve |
| 8,241,365 B2 | 8/2012 | Williams, Jr. et al. |
| 8,241,366 B2 | 8/2012 | Roche et al. |
| 8,246,621 B2 | 8/2012 | Poncet |
| 8,246,687 B2 | 8/2012 | Katrana et al. |
| 8,277,454 B2 | 10/2012 | Neubauer et al. |
| 8,277,511 B2 | 10/2012 | Tornier et al. |
| 8,282,685 B2 | 10/2012 | Rochetin et al. |
| 8,292,902 B2 | 10/2012 | Fenton |
| 8,303,665 B2 | 11/2012 | Tornier et al. |
| 8,308,806 B2 | 11/2012 | Grant et al. |
| 8,317,871 B2 | 11/2012 | Stone et al. |
| 8,323,347 B2 | 12/2012 | Guederian et al. |
| 8,357,163 B2 | 1/2013 | Sidebotham et al. |
| 8,357,201 B2 | 1/2013 | Mayer et al. |
| 8,361,147 B2 | 1/2013 | Shterling et al. |
| 8,366,713 B2 | 2/2013 | Long et al. |
| 8,366,780 B2 | 2/2013 | Klawitter et al. |
| 8,388,620 B2 | 3/2013 | Brunnarius |
| 8,388,683 B2 | 3/2013 | Hassler et al. |
| 8,409,294 B2 | 4/2013 | Divoux |
| 8,425,614 B2 | 4/2013 | Winslow et al. |
| 8,428,693 B2 | 4/2013 | Meulink |
| 8,449,548 B2 * | 5/2013 | Nelson ............... A61B 17/1604 606/86 R |
| 8,449,552 B2 | 5/2013 | Sanders |
| 8,449,617 B1 | 5/2013 | McDaniel et al. |
| 8,465,548 B2 | 6/2013 | Long |
| D685,474 S | 7/2013 | Courtney, Jr. et al. |
| 8,480,677 B2 | 7/2013 | Groh |
| 8,480,750 B2 | 7/2013 | Long |
| 8,486,076 B2 | 7/2013 | Chavarria et al. |
| 8,506,569 B2 | 8/2013 | Keefer et al. |
| 8,506,638 B2 | 8/2013 | Vanasse et al. |
| 8,523,867 B2 | 9/2013 | Rauscher et al. |
| 8,535,319 B2 | 9/2013 | Ball |
| 8,535,329 B2 | 9/2013 | Sarin et al. |
| 8,545,506 B2 | 10/2013 | Long et al. |
| 8,545,511 B2 | 10/2013 | Splieth et al. |
| 8,551,177 B2 | 10/2013 | De Wilde et al. |
| 8,556,901 B2 | 10/2013 | Anthony et al. |
| 8,579,984 B2 | 11/2013 | Borowsky |
| 8,585,706 B2 | 11/2013 | Lafosse et al. |
| 8,591,592 B2 | 11/2013 | Dreyfuss |
| 8,632,603 B2 | 1/2014 | Hodorek et al. |
| 8,636,801 B2 | 1/2014 | Hassler et al. |
| 8,657,820 B2 | 2/2014 | Kubiak et al. |
| 8,663,333 B2 | 3/2014 | Metcalfe et al. |
| 8,689,425 B2 | 4/2014 | Mutchler et al. |
| 8,690,951 B2 | 4/2014 | Baum et al. |
| 8,690,952 B2 | 4/2014 | Dallmann |
| 8,696,677 B2 | 4/2014 | Chavarria et al. |
| 8,696,680 B2 | 4/2014 | Iannotti et al. |
| 8,702,717 B2 | 4/2014 | Rauscher et al. |
| 8,702,800 B2 | 4/2014 | Linares et al. |
| 8,715,363 B2 | 5/2014 | Ratron et al. |
| 8,721,650 B2 | 5/2014 | Fanton et al. |
| 8,721,726 B2 | 5/2014 | Capon et al. |
| 8,721,727 B2 | 5/2014 | Ratron et al. |
| 8,747,481 B2 | 6/2014 | Maurer |
| 8,753,379 B1 | 6/2014 | Frei et al. |
| 8,753,390 B2 | 6/2014 | Shohat |
| 8,753,402 B2 | 6/2014 | Winslow et al. |
| 8,764,836 B2 | 7/2014 | De Wilde et al. |
| 8,771,362 B2 | 7/2014 | Isch et al. |
| 8,778,028 B2 | 7/2014 | Gunther et al. |
| 8,784,494 B2 | 7/2014 | Dro |
| 8,795,279 B2 | 8/2014 | Winslow et al. |
| 8,795,280 B2 | 8/2014 | Winslow et al. |

(56) References Cited

U.S. PATENT DOCUMENTS

| | | |
|---|---|---|
| 8,821,503 B2 | 9/2014 | Tornier et al. |
| 8,834,497 B2 | 9/2014 | Snell et al. |
| 8,840,671 B2 | 9/2014 | Ambacher |
| 8,852,283 B2 | 10/2014 | Tornier et al. |
| 8,858,640 B2 | 10/2014 | Brunnarius et al. |
| 8,864,834 B2 | 10/2014 | Boileau et al. |
| 8,870,962 B2 | 10/2014 | Roche et al. |
| 8,876,907 B2 | 11/2014 | Baptista et al. |
| 8,882,845 B2 | 11/2014 | Wirth et al. |
| 8,888,855 B2 | 11/2014 | Roche et al. |
| 8,920,428 B2 | 12/2014 | Zakaria et al. |
| 8,920,508 B2 | 12/2014 | Iannotti et al. |
| 8,932,361 B2 | 1/2015 | Tornier et al. |
| 8,945,138 B2 | 2/2015 | Klotz et al. |
| 8,945,229 B2 | 2/2015 | Lappin |
| 8,945,234 B2 | 2/2015 | Humphrey |
| 8,968,410 B2 | 3/2015 | Veronesi et al. |
| 8,974,536 B2 | 3/2015 | Walch et al. |
| 8,974,537 B2 | 3/2015 | Dreyfuss |
| 8,984,731 B2 | 3/2015 | Broeck et al. |
| 8,992,539 B2 | 3/2015 | Iannotti et al. |
| 8,998,994 B2 | 4/2015 | Winslow et al. |
| 9,033,990 B2 | 5/2015 | Iannotti et al. |
| 9,044,330 B2 | 6/2015 | Chavarria et al. |
| 9,056,013 B2 | 6/2015 | Faure et al. |
| 9,066,806 B2 | 6/2015 | Phipps |
| 9,078,673 B2 | 7/2015 | Fitzpatrick |
| 9,084,680 B2 | 7/2015 | Katrana et al. |
| 9,089,435 B2 | 7/2015 | Walch et al. |
| 9,113,918 B2 | 8/2015 | Chaney et al. |
| 9,119,643 B2 | 9/2015 | Winslow et al. |
| 9,125,702 B2 | 9/2015 | Witt |
| 9,132,016 B2 | 9/2015 | Flaherty et al. |
| 9,161,793 B2 | 10/2015 | Huebner |
| 9,161,843 B2 | 10/2015 | Anthony et al. |
| 9,173,665 B2 | 11/2015 | Couture |
| 9,173,742 B2 | 11/2015 | Faccioli et al. |
| D745,678 S | 12/2015 | Courtney et al. |
| 9,204,872 B2 | 12/2015 | Koepke |
| 9,211,191 B2 | 12/2015 | Grant et al. |
| 9,211,199 B2 | 12/2015 | Ratron |
| 9,226,830 B2 | 1/2016 | De Wilde et al. |
| 9,232,955 B2 | 1/2016 | Bonin, Jr. et al. |
| 9,241,804 B2 | 1/2016 | Iannotti |
| 9,248,022 B2 | 2/2016 | Lappin et al. |
| 9,254,155 B2 | 2/2016 | Iannotti et al. |
| 9,278,005 B2 | 3/2016 | Smits et al. |
| 9,283,076 B2 | 3/2016 | Sikora et al. |
| 9,283,083 B2 | 3/2016 | Winslow et al. |
| 9,289,218 B2 | 3/2016 | Courtney, Jr. et al. |
| 9,289,221 B2 | 3/2016 | Gelaude et al. |
| 9,289,253 B2 | 3/2016 | Vanasse et al. |
| 9,289,306 B2 | 3/2016 | Goldberg et al. |
| 9,301,812 B2 | 4/2016 | Kehres et al. |
| 9,320,527 B2 | 4/2016 | Kehres et al. |
| 9,320,608 B2 | 4/2016 | Sperling |
| 9,345,497 B2 | 5/2016 | Gonzalvez et al. |
| 9,351,743 B2 | 5/2016 | Kehres et al. |
| 9,351,744 B2 | 5/2016 | Kunz et al. |
| 9,351,844 B2 | 5/2016 | Walch et al. |
| 9,370,428 B2 | 6/2016 | Winslow et al. |
| 9,381,026 B2 | 7/2016 | Trouilloud et al. |
| 9,408,613 B2 | 8/2016 | Kehres et al. |
| 9,408,652 B2 | 8/2016 | Hassler et al. |
| 9,408,706 B2 | 8/2016 | Hassler et al. |
| 9,414,927 B2 | 8/2016 | Iannotti et al. |
| 9,421,021 B2 | 8/2016 | Keppler |
| 9,421,085 B2 | 8/2016 | Bindra et al. |
| 9,433,507 B2 | 9/2016 | Reubelt et al. |
| 9,433,508 B2 | 9/2016 | Phipps |
| 9,445,805 B2 | 9/2016 | Snell et al. |
| 9,451,973 B2 | 9/2016 | Heilman et al. |
| 9,474,619 B2 | 10/2016 | Reubelt et al. |
| 9,796,074 B2 * | 10/2017 | Mugnier ............... A61F 2/4607 |
| 2001/0014827 A1 | 8/2001 | Chambat et al. |
| 2003/0083751 A1 | 5/2003 | Tornier |
| 2003/0093080 A1 | 5/2003 | Brown et al. |
| 2003/0149485 A1 | 8/2003 | Tornier |
| 2003/0149486 A1 | 8/2003 | Huebner |
| 2003/0163135 A1 | 8/2003 | Hathaway |
| 2005/0060039 A1 | 3/2005 | Cyprien |
| 2005/0278030 A1 | 12/2005 | Tornier et al. |
| 2005/0278032 A1 | 12/2005 | Tornier et al. |
| 2005/0288791 A1 | 12/2005 | Tornier et al. |
| 2006/0020344 A1 | 1/2006 | Shultz et al. |
| 2006/0079963 A1 | 4/2006 | Hansen |
| 2006/0173457 A1 | 8/2006 | Tornier |
| 2006/0217737 A1 | 9/2006 | Iversen |
| 2006/0235538 A1 | 10/2006 | Rochetin et al. |
| 2007/0038302 A1 | 2/2007 | Shultz et al. |
| 2007/0043265 A1 | 2/2007 | Rochetin |
| 2007/0142840 A1 | 6/2007 | Goodwin et al. |
| 2007/0162025 A1 | 7/2007 | Tornier et al. |
| 2007/0173947 A1 | 7/2007 | Ratron et al. |
| 2007/0179625 A1 | 8/2007 | Ekholm et al. |
| 2007/0179628 A1 | 8/2007 | Rochetin |
| 2007/0225821 A1 | 9/2007 | Reubelt et al. |
| 2007/0244564 A1 | 10/2007 | Ferrand et al. |
| 2007/0244565 A1 | 10/2007 | Stchur |
| 2007/0250174 A1 | 10/2007 | Tornier et al. |
| 2007/0270718 A1 | 11/2007 | Rochetin et al. |
| 2008/0021564 A1 | 1/2008 | Gunther |
| 2008/0183297 A1 | 7/2008 | Boileau et al. |
| 2008/0188936 A1 | 8/2008 | Ball et al. |
| 2008/0255568 A1 | 10/2008 | Tornier et al. |
| 2009/0024135 A1 | 1/2009 | Triplett et al. |
| 2009/0048687 A1 | 2/2009 | Tornier et al. |
| 2009/0171462 A1 | 7/2009 | Poncet et al. |
| 2009/0254090 A1 | 10/2009 | Lizee |
| 2009/0270993 A1 | 10/2009 | Maisonneuve et al. |
| 2009/0287309 A1 | 11/2009 | Walch et al. |
| 2010/0125336 A1 | 5/2010 | Johnson et al. |
| 2010/0241235 A1 | 9/2010 | Basamania et al. |
| 2010/0268239 A1 | 10/2010 | Sikora et al. |
| 2010/0324691 A1 | 12/2010 | Brunnarius |
| 2011/0040303 A1 | 2/2011 | Iannotti |
| 2011/0046625 A1 | 2/2011 | Boileau et al. |
| 2011/0060417 A1 | 3/2011 | Simmen et al. |
| 2011/0082557 A1 | 4/2011 | Mutchler et al. |
| 2011/0119884 A1 | 5/2011 | Ratron |
| 2011/0125155 A1 | 5/2011 | Mutchler et al. |
| 2011/0125273 A1 | 5/2011 | Ratron et al. |
| 2011/0130795 A1 | 6/2011 | Ball |
| 2011/0152954 A1 * | 6/2011 | Nelson ............... A61B 17/1604 606/86 R |
| 2011/0166661 A1 | 7/2011 | Boileau et al. |
| 2011/0178604 A1 | 7/2011 | Porter |
| 2011/0196491 A1 | 8/2011 | Huebner |
| 2011/0224663 A1 | 9/2011 | Heim et al. |
| 2011/0224673 A1 | 9/2011 | Smith |
| 2011/0238113 A1 | 9/2011 | Fanton et al. |
| 2011/0295254 A1 | 12/2011 | Brunnarius |
| 2011/0295375 A1 | 12/2011 | Appenzeller et al. |
| 2012/0071985 A1 | 3/2012 | Hodorek et al. |
| 2012/0078258 A1 | 3/2012 | Lo et al. |
| 2012/0109137 A1 | 5/2012 | Iannotti et al. |
| 2012/0123419 A1 | 5/2012 | Purdy et al. |
| 2012/0130433 A1 | 5/2012 | Huebner |
| 2012/0141034 A1 | 6/2012 | Iannotti et al. |
| 2012/0143267 A1 | 6/2012 | Iannotti et al. |
| 2012/0191210 A1 | 7/2012 | Ratron et al. |
| 2012/0209390 A1 | 8/2012 | Gosset et al. |
| 2012/0209392 A1 | 8/2012 | Angibaud et al. |
| 2012/0239042 A1 | 9/2012 | Lappin et al. |
| 2012/0239043 A1 | 9/2012 | Lappin |
| 2012/0253467 A1 | 10/2012 | Frankle |
| 2012/0259339 A1 | 10/2012 | Hood et al. |
| 2012/0276509 A1 | 11/2012 | Iannotti et al. |
| 2012/0290098 A1 | 11/2012 | Mutchler et al. |
| 2012/0290272 A1 | 11/2012 | Bryan |
| 2013/0012963 A1 | 1/2013 | Harrington et al. |
| 2013/0023998 A1 | 1/2013 | Pandya |
| 2013/0023999 A1 | 1/2013 | Gregory |
| 2013/0053968 A1 | 2/2013 | Nardini et al. |

(56) References Cited

U.S. PATENT DOCUMENTS

| | | |
|---|---|---|
| 2013/0060341 A1 | 3/2013 | Tornier et al. |
| 2013/0066321 A1 | 3/2013 | Mannss et al. |
| 2013/0066322 A1 | 3/2013 | Chana |
| 2013/0071358 A1 | 3/2013 | Peterson et al. |
| 2013/0079782 A1 | 3/2013 | Cournoyer |
| 2013/0116797 A1 | 5/2013 | Coulange et al. |
| 2013/0123930 A1 | 5/2013 | Burt |
| 2013/0144394 A1 | 6/2013 | Hassler et al. |
| 2013/0197528 A1 | 8/2013 | Zakaria et al. |
| 2013/0261751 A1 | 10/2013 | Lappin |
| 2013/0267960 A1 | 10/2013 | Groh |
| 2013/0338673 A1 | 12/2013 | Keppler |
| 2014/0005789 A1 | 1/2014 | Chavarria et al. |
| 2014/0025173 A1 | 1/2014 | Cardon et al. |
| 2014/0039632 A1 | 2/2014 | Hollis |
| 2014/0058523 A1 | 2/2014 | Walch et al. |
| 2014/0066933 A1 | 3/2014 | Ek et al. |
| 2014/0081270 A1 | 3/2014 | Klotz et al. |
| 2014/0107652 A1 | 4/2014 | Walker |
| 2014/0128983 A1 | 5/2014 | Flaherty et al. |
| 2014/0142578 A1 | 5/2014 | Hananouchi et al. |
| 2014/0188233 A1 | 7/2014 | Mutchler et al. |
| 2014/0194995 A1 | 7/2014 | Koka |
| 2014/0214170 A1 | 7/2014 | Ratron et al. |
| 2014/0236304 A1 | 8/2014 | Hodorek et al. |
| 2014/0243827 A1 | 8/2014 | Boileau et al. |
| 2014/0257304 A1 | 9/2014 | Eash |
| 2014/0276838 A1 | 9/2014 | Tsukayama et al. |
| 2014/0276850 A1 | 9/2014 | Chaney et al. |
| 2014/0288597 A1 | 9/2014 | Fanton et al. |
| 2014/0296911 A1 | 10/2014 | Fanton et al. |
| 2014/0343572 A1 | 11/2014 | Windolf et al. |
| 2015/0073424 A1 | 3/2015 | Couture et al. |
| 2015/0119891 A1 | 4/2015 | Goldberg et al. |
| 2015/0127104 A1 | 5/2015 | Levy et al. |
| 2015/0150688 A1 | 6/2015 | Vanasse et al. |
| 2015/0157462 A1 | 6/2015 | Ek et al. |
| 2015/0190151 A1 | 7/2015 | Budhabhatti et al. |
| 2015/0223941 A1 | 8/2015 | Lang |
| 2015/0250601 A1 | 9/2015 | Humphrey |
| 2015/0257769 A1 | 9/2015 | Papenfuss |
| 2015/0257772 A1 | 9/2015 | Papenfuss |
| 2015/0265288 A1 | 9/2015 | Guederian |
| 2015/0289985 A1 | 10/2015 | Hopkins |
| 2015/0305877 A1 | 10/2015 | Gargac et al. |
| 2015/0328015 A1* | 11/2015 | Olson .................. A61F 2/46 606/102 |
| 2015/0335440 A1 | 11/2015 | Linares et al. |
| 2015/0335441 A1 | 11/2015 | Linares et al. |
| 2015/0342620 A1 | 12/2015 | Winslow |
| 2015/0342622 A1 | 12/2015 | Kehres et al. |
| 2015/0342743 A1 | 12/2015 | Sobky |
| 2015/0359544 A1 | 12/2015 | Pressacco et al. |
| 2015/0374387 A1 | 12/2015 | Courtney, Jr. et al. |
| 2015/0374502 A1 | 12/2015 | Hodorek et al. |
| 2016/0030187 A1 | 2/2016 | Sperling et al. |
| 2016/0030196 A1 | 2/2016 | Eraly et al. |
| 2016/0038203 A1 | 2/2016 | Huebner |
| 2016/0045323 A1 | 2/2016 | Kovacs et al. |
| 2016/0074047 A1 | 3/2016 | Fritzinger et al. |
| 2016/0074052 A1 | 3/2016 | Keppler et al. |
| 2016/0089163 A1 | 3/2016 | Eash et al. |
| 2016/0113645 A1 | 4/2016 | Hardy et al. |
| 2016/0135818 A1 | 5/2016 | Weekes et al. |
| 2016/0143749 A1 | 5/2016 | Holovacs et al. |
| 2016/0199074 A1 | 7/2016 | Winslow et al. |
| 2016/0242933 A1 | 8/2016 | Deransart et al. |
| 2016/0256222 A1 | 9/2016 | Walch |
| 2016/0270922 A1 | 9/2016 | Pressacco et al. |
| 2016/0287266 A1 | 10/2016 | Sikora et al. |
| 2016/0287400 A1 | 10/2016 | Muir et al. |
| 2016/0287401 A1 | 10/2016 | Muir et al. |
| 2016/0296285 A1 | 10/2016 | Chaoui et al. |

OTHER PUBLICATIONS

Global FX, Surgical Technique, 2009, pp. 1-44.
Zimmer, Zimmer Trabecular Metal Reverse Shoulder System . Surgical Technique 2010.

* cited by examiner

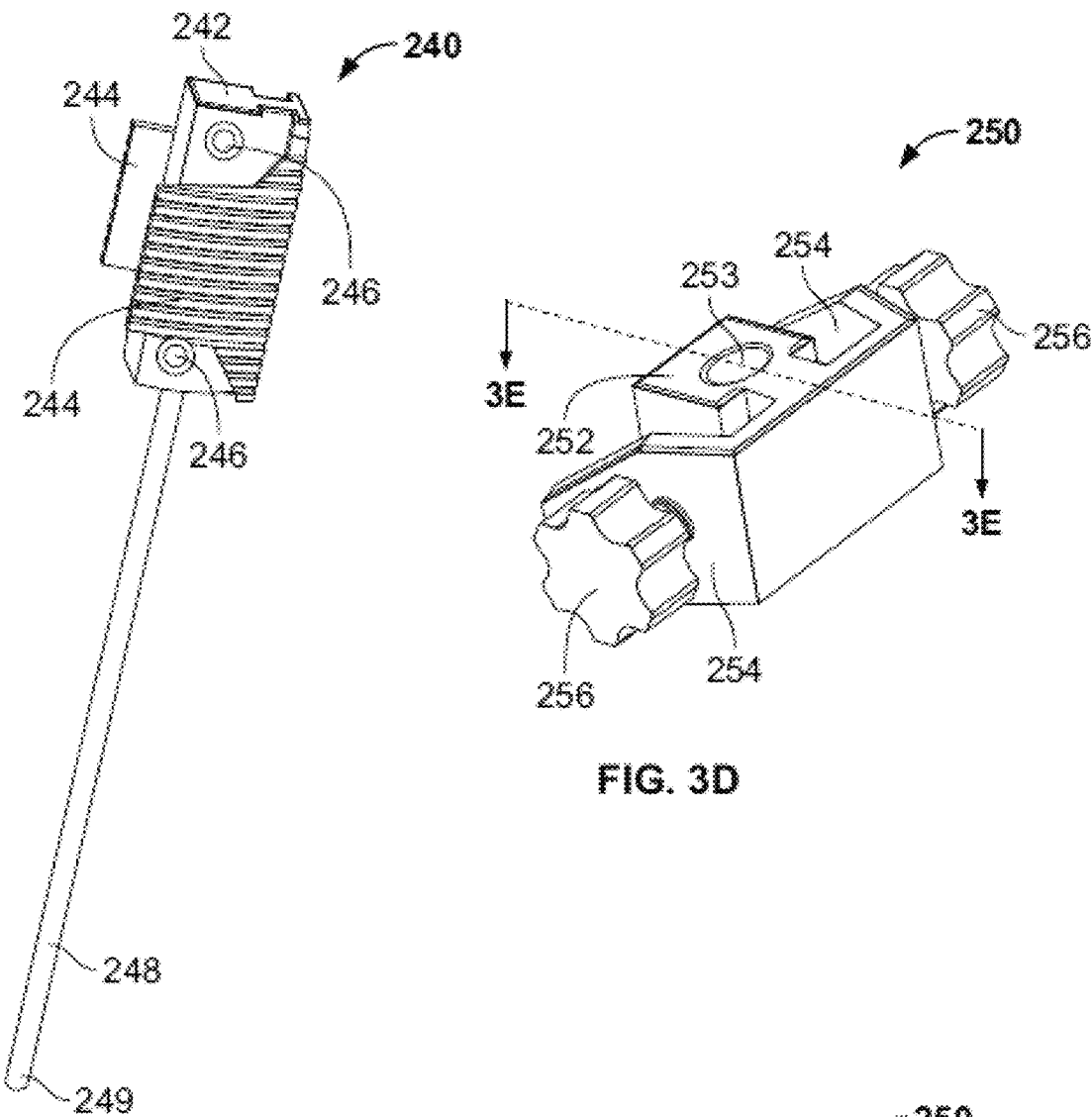
FIG. 3C
FIG. 3D
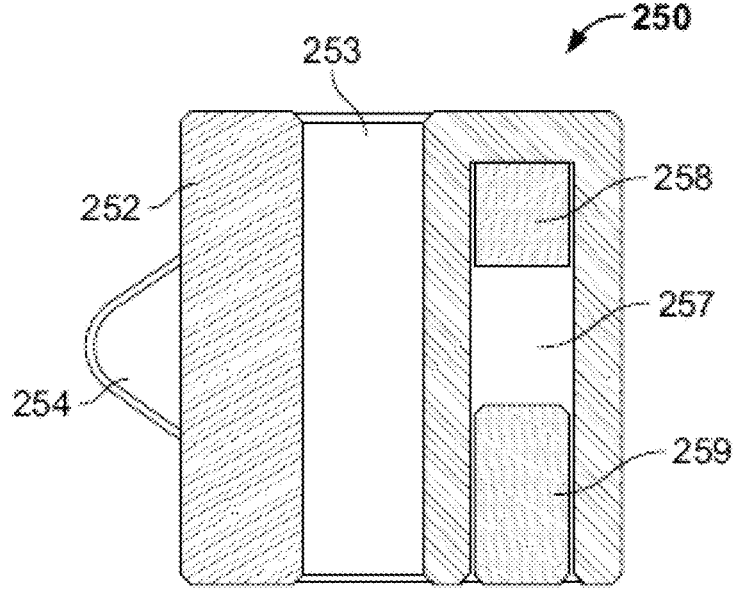
FIG. 3E

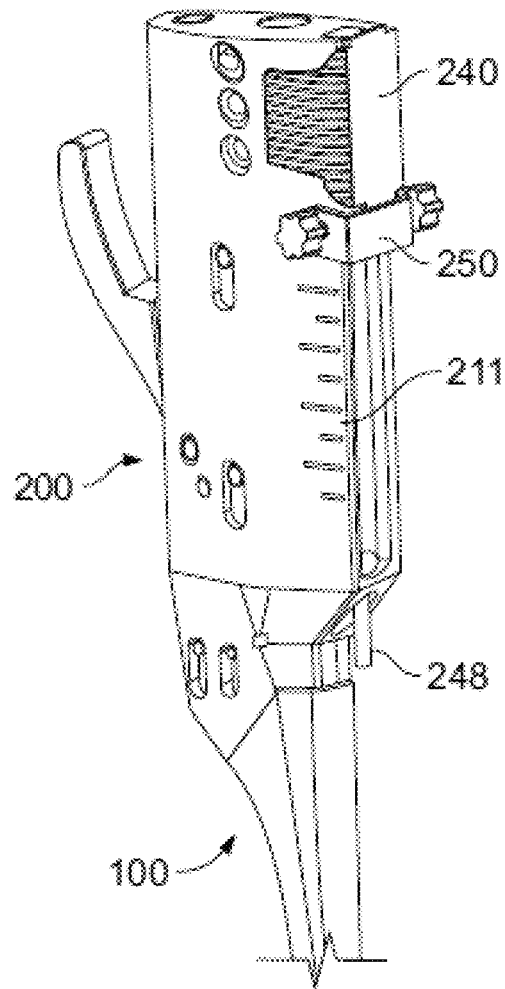
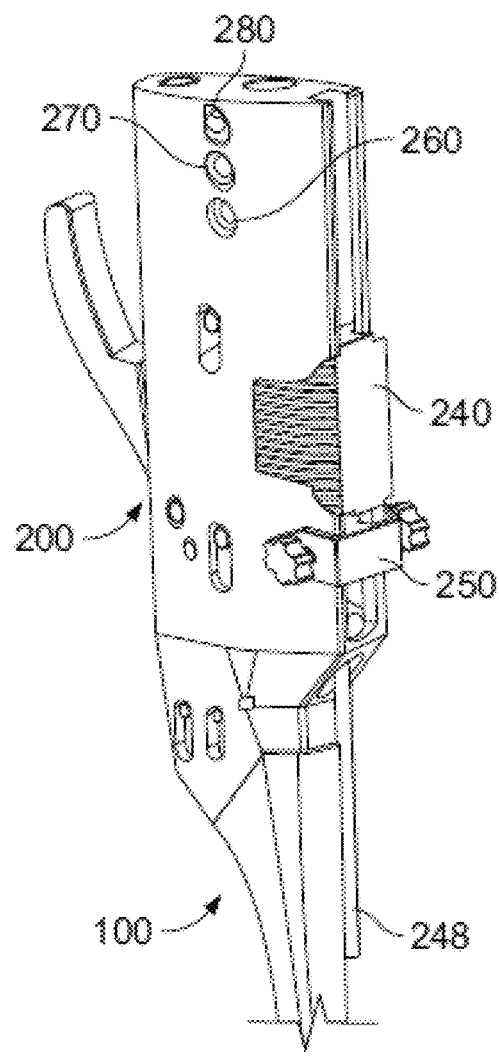
FIG. 4A
FIG. 4B

GUIDES FOR FRACTURE SYSTEM

CROSS-REFERENCE TO RELATED APPLICATIONS

This application is a continuation-in-part of U.S. patent application Ser. No. 14/279,572, filed on May 16, 2014, the disclosure of which is hereby incorporated by reference herein

FIELD OF THE INVENTION

The present invention relates to guides for determining a desired position and orientation of an implant in a fracture setting, and in particular relates to guides for gauging the height and/or orienting the version of an implant with respect to at least one bone fragment.

BACKGROUND OF THE INVENTION

A joint replacement procedure is sometimes necessary to repair a joint having a diseased or damaged articular surface. Such a procedure may involve removal of the diseased or damaged portions of the joint and replacing them with a prosthetic implant. This is often a desirable procedure for ball-and-socket type joints, particularly the shoulder and hip joints. A shoulder joint replacement procedure, for example, often involves removal of the humeral head and replacement thereof with an implant including a stem and a head. It is important that the implant be positioned correctly within the joint in order to ensure that appropriate joint kinematics, including range of motion, are preserved so as to replicate, as closely as possible, those of the original joint.

The structure of prosthetic joint components has been developed to be suited for permanent implantation into the joint and includes features that may promote bony ingrowth, adhesion using cement, press-fit or a combination thereof. Particularly, in the case of implants including a stem, such as those used in shoulder arthroplasty, these features are generally included on the outside surface of the stem. Such features may not be well-suited for use during the assessment of joint kinematics. Accordingly, instruments such as trials have been developed to be used in this part of the procedure. Generally, trials are affixed to the bone during joint kinematic evaluation and removed therefrom after a proper position for the implant has been determined.

Typically, trials are designed to correspond to an implant in size and shape. In a shoulder arthroplasty procedure, for example, a trial may be designed to be temporarily inserted into a prepared medullary canal of the humerus in a manner similar to that of an implant. Known trials may take many forms. For example, an expanding trial stem, such as that described in U.S. Pat. No. 8,216,320, the entire contents of which are hereby incorporated by reference herein, includes a stem that may be expanded after insertion into the medullary canal. When using such trial stems, particularly in shoulder replacements, it may be difficult to establish the proper position and orientation for the implant in the humerus. It would thus be desirable to have guides that simplify the determination of proper positioning of the implant during use of a trial stem.

BRIEF SUMMARY OF THE INVENTION

According to one aspect of the disclosure, a prosthetic shoulder implant system includes a prosthetic humeral implant and a version device for measuring a rotational position of the prosthetic humeral implant. The prosthetic humeral implant includes a catch member aperture and a first locking pin aperture. The version device includes a rotatable member, a plate, and a first locking pin. The rotatable member has a body and a flexure member. The plate has a catch member adapted to mate with the catch member aperture, and a projection in contact with the flexure member, the catch member extending from a distal portion of the version device along a first axis. The first locking pin extends from the distal portion of the version device along a second axis non-parallel to the first axis and is adapted to mate with the first locking pin aperture. In an unlocked condition of the system, the rotatable member has a first rotated position in which the flexure member is in an uncompressed state and the plate is in a first position. In a locked condition of the system, the rotatable member has a second rotated position in which the flexure member is in a compressed state and the plate is in a second position proximal of the first position.

The prosthetic humeral implant may be a permanent implant stem that includes a plurality of indicia for marking the height of the permanent implant stem. The prosthetic humeral implant may be a trial stem implant that includes a plurality of indicia for marking the height of the trial stem implant. A biasing member may bias the plate to the first position. The body of the rotatable member may include a first projection in contact with a stopper pin when the rotatable member is in the first rotated position, the first projection resisting rotation of the rotatable member in a first rotational direction. The body of the rotatable member may include a second projection in contact with the stopper pin when the rotatable member is in the second rotated position, the second projection resisting rotation of the rotatable member in a second rotational direction opposite the first rotational direction.

The flexure member may include a first groove, a second groove, and a projecting portion between the first and second grooves. In the unlocked condition of the system, the projection of the plate may be positioned within the first groove. In the locked condition of the system, the projection of the plate may be positioned within the second groove. The system may include an intermediate condition in which the rotatable member is in a third rotated position between the first and second rotated positions and the projection of the plate contacts the projecting portion of the flexure member. The flexure member may be at a maximum amount of compression in the intermediate condition of the system.

When the catch member is positioned within the catch member aperture, the first locking pin is positioned within the first locking pin aperture, and the system is in the locked condition, a compressive force may be maintained between the version device and the prosthetic humeral implant. The version device may include a plurality of version rod apertures. The version rod apertures may be threaded apertures configured to mate with a version rod. Each of the plurality of version rod apertures may be angled differently than each other version rod aperture. The plate may include a first slot and the version device may include a first plate pin positioned within the first slot. The first plate pin may guide movement of the plate between the first position of the plate and the second position of the plate. The prosthetic humeral implant may be a permanent implant stem, and the system may further include a trial stem including a trial catch member aperture adapted to mate with the catch member, and a trial first locking pin aperture adapted to mate with the first locking pin aperture, the permanent implant stem including a plurality of height indicia corresponding to a plurality of height indicia of the trial stem.

BRIEF DESCRIPTION OF THE DRAWINGS

FIG. 3C is an isolated perspective view of a slider member of the height measuring gauge of FIG. 3A.

FIG. 3D is an isolated perspective view of a support member or pointer of the height measuring gauge of FIG. 3A.

FIG. 3E is a cross-sectional view of the pointer taken along line 3E-3E in FIG. 3D.

FIG. 4A is a perspective view of the trial stem of FIG. 2 attached to the height measuring gauge of FIG. 3 in a locked configuration with the pointer and slider in a neutral or first position.

FIG. 4B is a perspective view of the trial stem of FIG. 2 attached to the height measuring gauge of FIG. 3 in a locked configuration with the pointer and slider in an active or second position.

DETAILED DESCRIPTION

In describing preferred embodiments of the disclosure, reference will be made to the directional nomenclature used in describing the human body. It is noted that this nomenclature is used only for convenience and that it is not intended to be limiting with respect to the scope of the invention. When referring to specific directions in relation to a device, the device is understood to be described only with respect to its orientation and position during an exemplary application to the human body. As used herein when referring to bones or other parts of the body, the term "proximal" means closer to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body. Further, although the devices and methods described herein are generally described in relation to human shoulder replacements, it should be understood that the devices and methods are not intended to be so limited and could be used with other joints, such as other ball and socket joints, including the hip, for example.

Figure 1:
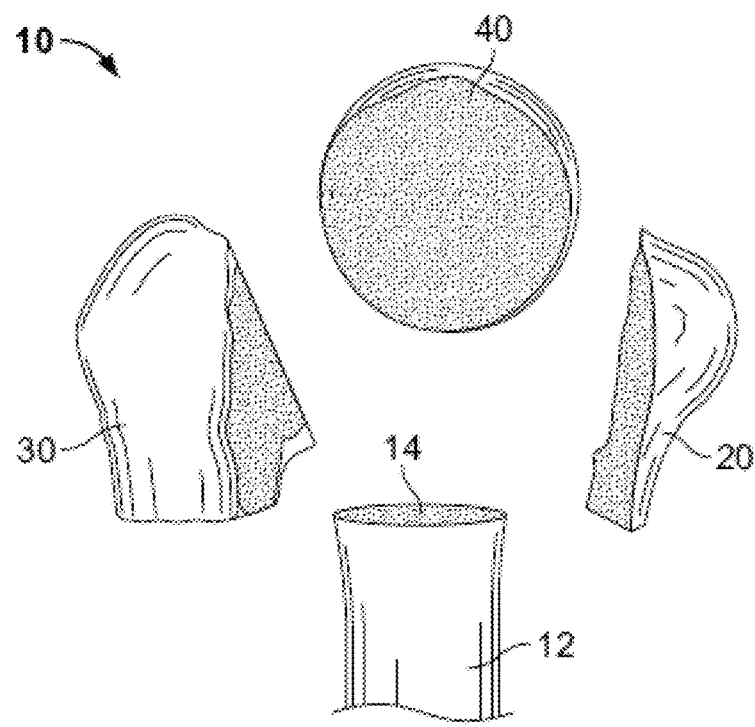
FIG. 1 is a schematic view of an exemplary proximal humerus broken into a plurality of bone fragments.

Generally, the replacement of a humeral head with a prosthetic implant during shoulder arthroplasty involves gaining access to the shoulder joint through a retracted incision and removing the damaged humeral head. An exemplary damaged proximal humerus 10 is illustrated in FIG. 1. Although such breaks giving rise to a plurality of bone fragments may occur in any number of ways, this particular humerus 10 is broken such that a first segment 20, a second segment 30, and a third segment 40 including a substantial portion of the humeral head are each detached from the proximal end 12 of the humerus. After removal of the humeral head 40, the proximal end of the humeral medullary canal may be shaped in order to accept an implant according to known methods. In one exemplary method, a hand reamer, for example, may be used at a proximal humeral bearing surface 14 to remove bone material until an appropriately-shaped opening is formed in the proximal end 12 of humerus 10 for receiving an implant. Typically, successive reamers of increasing size are used in order to form an opening of the desired size. In many cases, bearing surface 14 may not be as flat as shown. Most surfaces at a fracture site are irregularly shaped unless there is a clean break between adjacent fragments. Such a surface may be resected into a generally flat shape to receive a corresponding bearing surface of a trial and/or implant stem as shown in FIG. 1.

Figure 2:
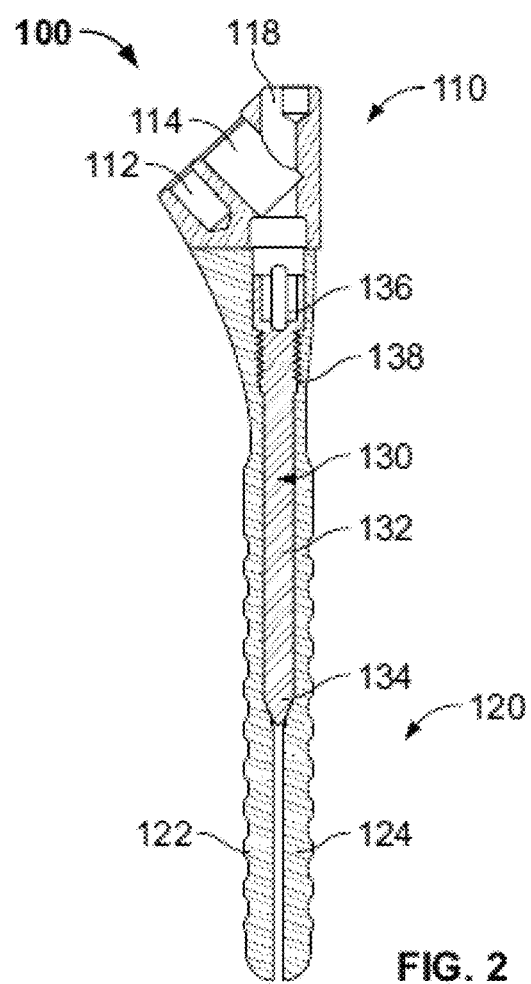
FIG. 2 is a cross-sectional view of one embodiment of a trial stem for use during a shoulder replacement procedure.

Once an appropriate bearing surface 14 and opening is formed for receiving an implant, trialing is conducted to determine the proper size and location for the implant prior to implantation thereof. According to one example of the present disclosure, trialing includes inserting a trial stem 100, as illustrated in FIG. 2, into the opening in the proximal end 12 of humerus 10. Trial stem 100 may include a proximal portion 110 connected to a distal portion 120, for example by welding, with an expansion bolt 130 positioned within the trial stem. Generally, proximal portion 110 is adapted for insertion into the proximal end 12 of a prepared humerus 10. Proximal portion 110 may include a catch aperture 112, a trial recess 114, two locking pin apertures (not visible in FIG. 2), and a driver recess 118. Catch aperture 112 and the locking pin apertures may be configured to mate with corresponding features on a height measuring gauge 200, for example, as described in greater detail below with respect to FIG. 3A. Trial recess 114 may be shaped to receive a corresponding portion of a trial humeral head (not shown) or a reverse cup humeral trial, such as that described in U.S. Pat. No. 8,545,511, the entire contents of which are hereby incorporated by reference herein. Trial recess 114 may have a longitudinal axis that is angled with respect to a longitudinal axis of distal portion 120 so as to substantially replicate the typical geometry of a shaft and neck of the native bone prior to a fracture situation as shown in FIG. 1.

The distal portion 120 of trial stem 100 may be structured to fit within a prepared bone canal, preferably the medullary canal of the humerus 10. Distal portion 120 projects along a longitudinal axis thereof from proximal portion 110 generally in the proximal-to-distal direction. Distal portion 120 may include a first arm 122 and a second arm 124 configured to move away from each other in cooperation with expansion bolt 130, such as that described in U.S. Pat. No. 8,216,320, the entire contents of which are hereby incorporated by reference herein. Distal portion 120, or a portion thereof, may define a cavity or be configured to accept expansion bolt 130, the cavity including a mating surface such as threads.

Expansion bolt 130 may generally include a shaft 132 with a pointed distal tip 134. A proximal end of expansion bolt 130 may include a head 136, which may include a recess, such as a hex recess, to cooperate with a correspondingly shaped driving tool (not shown). A proximal end of shaft 132 may include a mating surface, such as threads 138, configured to mate with a corresponding surface in the cavity of distal portion 120. Although proximal portion 110, distal portion 120, and expansion bolt 130 may each be separate pieces prior to assembly, trial stem 100 is preferably provided to the end user as a single piece with the proximal and distal portions permanently connected, for example by welding, with the expansion bolt contained therein.

After trial stem 100, which may be one chosen from a set of differently sized trial stems, is inserted into the opening in the proximal end 12 of humerus 10, the trial stem may be temporarily secured into place by expanding the distal portion 120. To expand the distal portion 120, a user may insert a driving tool (not shown) through driver recess 118 in the proximal portion 110 of the trial stem until the driving tool mates with the corresponding surface of the head 136 of expansion bolt 130. Rotating the driving tool may engage the threads 138 of expansion bolt 130 with corresponding threading in distal portion 120, driving the expansion bolt distally and causing first arm 122 to be separated from second arm 124, thus causing expansion of the distal end of distal portion 120. This expansion may result in a tighter fit of trial stem 100 in humerus 10. Geometrical stops may be included in one or both of expansion bolt 130 and distal portion 120 to limit the distance which the expansion bolt my travel in the proximal-to-distal direction. For example, the size of head 136 or a portion of the proximal shaft of expansion bolt 130 may be larger than certain portions of the cavity in the distal portion 120 of trial stem 100, such that advancement of the expansion bolt is limited to a particular range of movement.

Figure 3A:
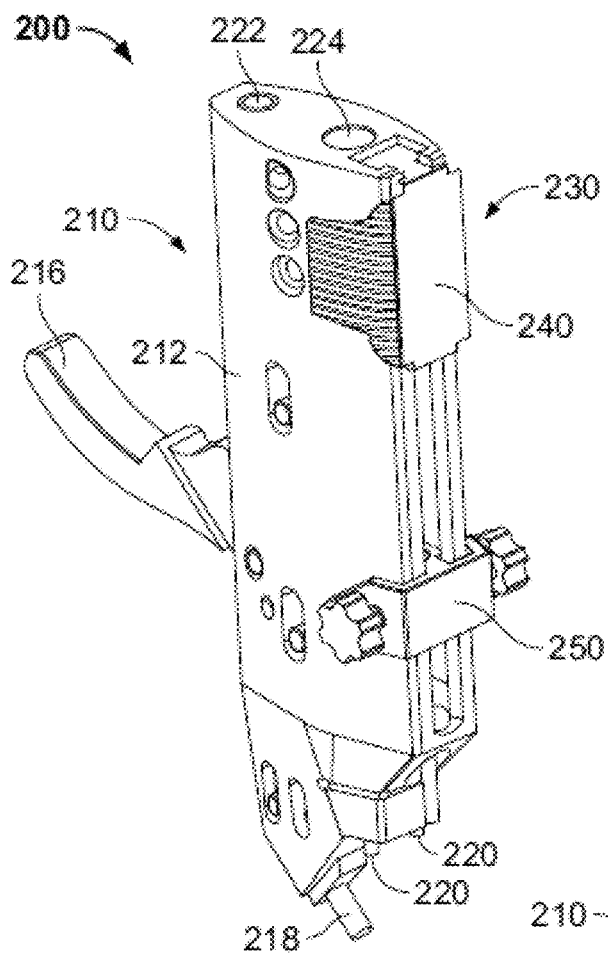
FIG. 3A is a perspective view of one embodiment of a height measuring gauge according to aspects of the disclosure.
Figure 3B:
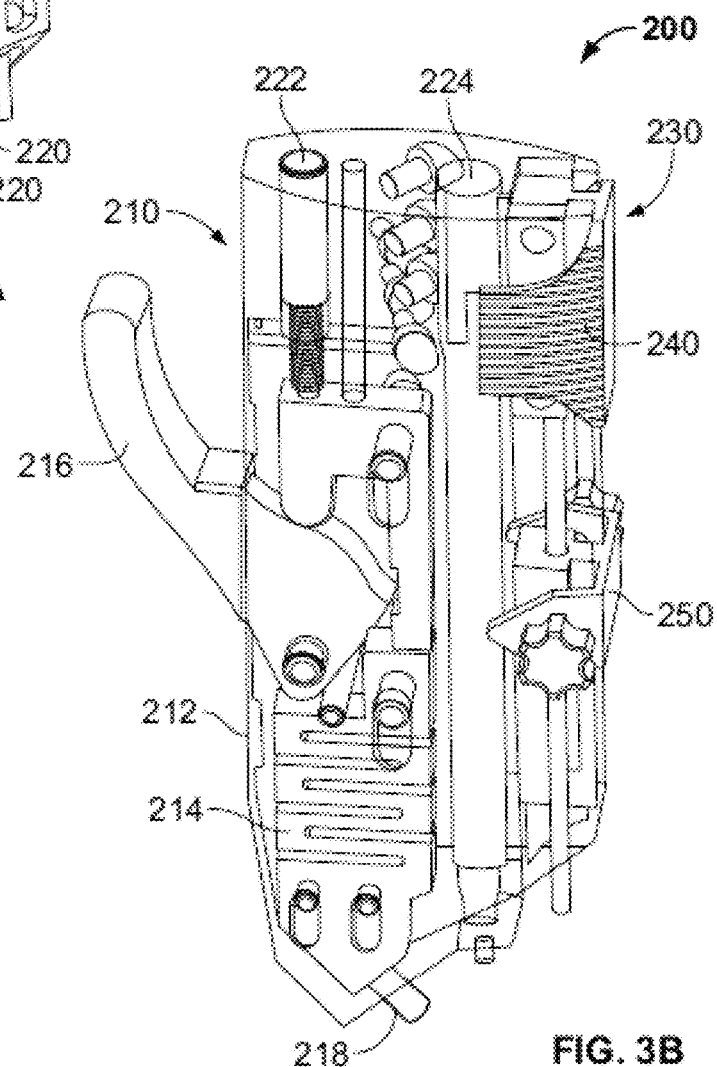
FIG. 3B is a perspective view of the height measuring gauge of FIG. 3A shown in partial transparency.

According to known methods, a height of trial stem 100 with respect to the medullary canal of the humerus 10 in which the trial stem is positioned may be noted by a user by, for example, observing indicia printed or otherwise marked on the trial stem with respect to bearing surface 14, for example. This height would be noted to ensure proper placement of a corresponding humeral stem implant. However, in another embodiment according to the present disclosure, a height measuring gauge 200, as illustrated in FIGS. 3A-B, may be connected to trial stem 100 prior to insertion into the medullary canal, and then used to insert trial stem into the medullary canal and to objectively mark the height of the trial stem with respect to a location or surface of the intact humerus, such as bearing surface 14, for example. Height measuring gauge 200 may include a handle portion 210 which may have a flexure spring assembly similar to the broach handle described in U.S. Pat. No. 8,449,548 ("the '548 Patent"), the entire contents of which are hereby incorporated by reference. Handle portion 210 may generally include a handle body 212, a deformable plate 214 positioned at least partially within handle body 212, and a loading member 216 configured to interact with the deformable plate. A distal end of deformable plate 214 may include a catch element 218 extending therefrom, and a distal end of handle body 212 may include a pair of locking pins 220 extending therefrom. Briefly, as a user actuates loading member 216 by rotating the loading member clockwise (transition illustrated from FIG. 3A to FIG. 3B), a cam on the loading member interacts with deformable plate 214, generally pushing the plate proximally. If handle portion 210 is not attached to any device, such actuation will not deform deformable plate 214. However, when catch element 218 is positioned inside catch aperture 112 of trial stem 100 and locking pins 220 are positioned inside the locking pin apertures of the trial stem, actuating loading member 216 causes the deformable plate 214 to deform, locking the trial stem to the handle portion 210 of height measuring gauge 200. This mechanism is described in greater detail in the '548 Patent.

It should be noted that a stabilizing mechanism, such as a pin 222 extending from a proximal portion of deformable plate 214 and fixed within a corresponding cavity defined by handle body 212, for example by welding, may be provided to apply a downward force on deformable plate 214. Pin 222 may be fixed to body 212 while deformable plate 214 is under some amount of compression. This configuration of pin 222 and deformable plate 214 may, for example, stabilize deformable plate 214 so that it does not move or "rattle" around within body 212 when loading member 216 is placing little or no force on deformable plate 214. It should further be noted that handle body 212 may include a driver aperture 224 extending the length of the body and configured to align with driver recess 118 of trial stem 100, such that when handle portion 210 is attached to the trial stem, a driving tool may be passed through the handle body, through the proximal portion 110 of the trial stem, and into the head 136 of expansion bolt 130 to allow driving of the expansion bolt.

Height measuring gauge 200 may also include a height measurement system 230. Height measurement system 230 may generally include a slider 240 and a height reference member in the form of pointer 250. Slider 240, illustrated alone in FIG. 3C, may generally include a main body 242, flanges 244, one or more ball plungers 246, and a bone position indicator 248 extending distally from the main body. The bone position indicator 248 may take the general form of an elongated slender cylindrical rod and may be integral or monolithic with slider 240. Main body 242 may include a relatively large portion configured to fit within a track defined by handle body 212, and a relatively small portion configured to extend through the track to the outside of the handle body. This configuration is illustrated as generally rectangular members fitting within rectangular grooves, but may take other forms, such as a dovetail configuration. This configuration provides main body 242 the ability to slide proximally or distally down the track in handle body 212 while being securely maintained therein. At least one flange 244, and preferably two, may extend from main body 242 and be configured to wrap around an outer portion of handle body 212. Flanges 244 may include texturing, such as ridges, to provide a gripping surface for a user. One or more ball plungers 246 may be imbedded in main body 242. In the illustrated configuration, a first pair of ball plungers 246 is positioned on a proximal end of main body 242 (only one visible in FIG. 3C) and another pair of ball plungers 246 is positioned on a distal end of the main body (only one visible in FIG. 3C). Generally, each ball plunger 246 may be spherical and biased away from main body 242 by a spring or spring-like member, although such biasing is not required. The ball plungers 246 may contact a wall of the track in handle body 242, providing frictional engagement therewith. A user may grip one or more flanges 244 to slide the slider 240 proximally or distally along the track, with ball plungers 246 facilitating such sliding motion while also providing friction to keep main body 242 generally in place when a sliding force is not being provided by a user. In other words, ball plungers 246 help prevent free sliding of slider 240 when no force is being applied to the slider. As will be explained in greater detail below, sliding main body 242 also slides bone position indicator 248, which may be used to determine a position of the humerus 10, and in particular the bearing surface 14 of the proximal portion 12 of the humerus.

The pointer 250 of height measurement system 230, illustrated alone in FIG. 3D, may generally include a main body 252, flanges 254, and one or more knobs 256. Main body 252 may be of a similar shape to the main body 242 of slider 240, with a relatively large portion configured to fit within a track defined by handle body 212, and a relatively small portion configured to extend through the track to the outside of the handle body. Main body 252 may also include an aperture 253 extending the length of the main body in a proximal-to-distal direction, the aperture being sized and configured to accept the bone position indicator 248 of slider 240 therethrough. At least one flange 254, and preferably two, may extend from main body 252 and be configured to wrap around an outer portion of handle body 212. Each flange 254 may include a knob 256. Knobs 256 may include threaded screws such that rotating the knobs in one direction drives the screws toward the center of pointer 250. When pointer 250 is connected to handle portion 210 such that main body 252 is positioned inside the track defined by handle body 212 and flanges 254 are on the outside of the handle portion, rotating the knobs 256 may cause the threaded screws to drive into frictional engagement with the handle body, causing the pointer to lock in its current position.

FIG. 3E illustrates a cross sectional view of pointer 250 taken along the line 3E-3E of FIG. 3D. A portion of main body 252 adjacent aperture 253 may define a cavity 257. Cavity 257 may include a magnet 258 and a cap 259, the cap acting to keep the magnet within the cavity. Magnet 258 is configured to cause engagement between a distal facing surface of the main body 242 of slider 240 and a proximal facing surface of pointer 250, such that during sliding motion of the slider, the pointer will slide along with the slider as long as the pointer is in an unlocked configuration. The coupled movement of the slider 240 with respect to the pointer 250 may be referred to as a first mode of operation. When slider 240 is at a desired location, as will be explained in greater detail below, pointer 250 will be at a corresponding desired location. At this point, the one or more knobs 256 may be rotated or tightened to keep pointer 250 in the desired location, with slider 240 removed. The frictional force of knobs 256 with handle body 212 is preferably greater than the attractive force between magnet 258 and the distal portion of the main body 242 of slider 240, such that removing the slider 242 does not cause pointer 250 to change positions once the pointer is in the locked configuration. The decoupled movement of the slider 240 with respect to the pointer 250 may be referred to as a second mode of operation.

As noted above, in an embodiment according to the present disclosure, height measurement gauge 200 may be connected to trial stem 100 prior to insertion into the medullary canal, and then used to insert the trial stem into the medullary canal and to objectively mark the height of the trial stem. Once height measuring gauge 200 is locked onto trial stem 100, as described above and illustrated in FIG. 4A, the trial stem is inserted into the previously formed opening to the medullary canal in the proximal portion 12 of humerus 10. If the user determines that a different sized trial stem 100 is desirable at this point, the user may remove the height measuring gauge 200 and trial stem 100, disconnect the original trial stem, and attach a differently sized trial stem to the height measuring gauge. If the trial stem 100 is an appropriate size, the user may continue. At this point, slider 240 and pointer 250 are in a first or initial proximal position, with the pointer attached to the slider via magnet 258 as described above. Pointer 250 is also in an unlocked configuration. To facilitate the initial choice of an appropriately sized trial stem 100, handle 210 may include a plurality of indicia, such as gradations 211 (only illustrated in FIG. 4A) that may referenced in concert with a contralateral X-ray template of the healthy bone. The contralateral X-ray template may include corresponding markings as handle 210 to facilitate the choice of an appropriately sized stem 100.

Once trial stem 100 is inserted into humerus 10 to a desirable depth as determined by the user, a driving tool may be inserted through the driver aperture 224 in handle portion 210, through driver recess 118 of the proximal portion 110 of trial stem 100, and finally mate the driving tool with the head 136 of expansion bolt 130. The driving tool may be rotated, torqued, or otherwise used to drive expansion bolt 130, causing expansion of the first and second arms 122, 124 of the distal portion 120 of trial stem 100, causing the trial stem to have a snug fit within the proximal portion 12 of humerus 10.

Figure 4C:
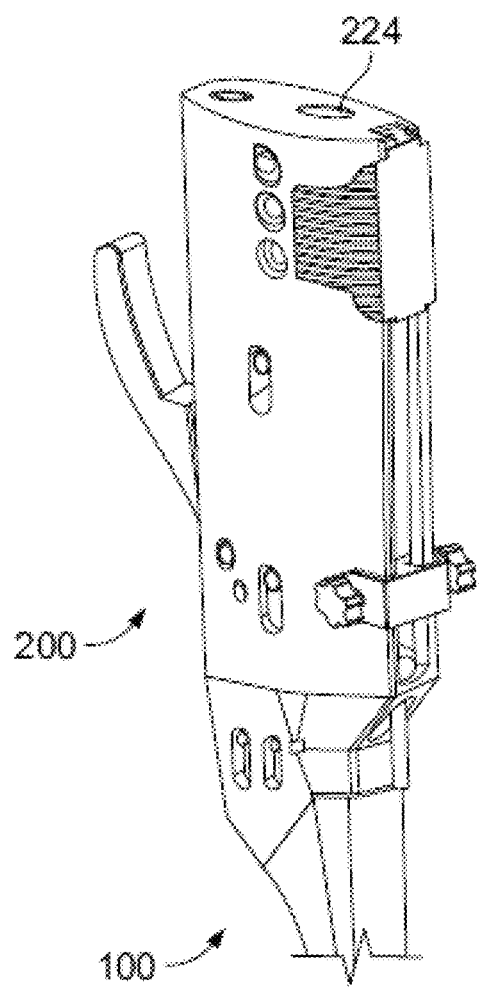
FIG. 4C is a perspective view of the trial stem of FIG. 2 attached to the height measuring gauge of FIG. 3 in a locked configuration with the pointer in the second position and the slider in the first position.
Figure 4D:
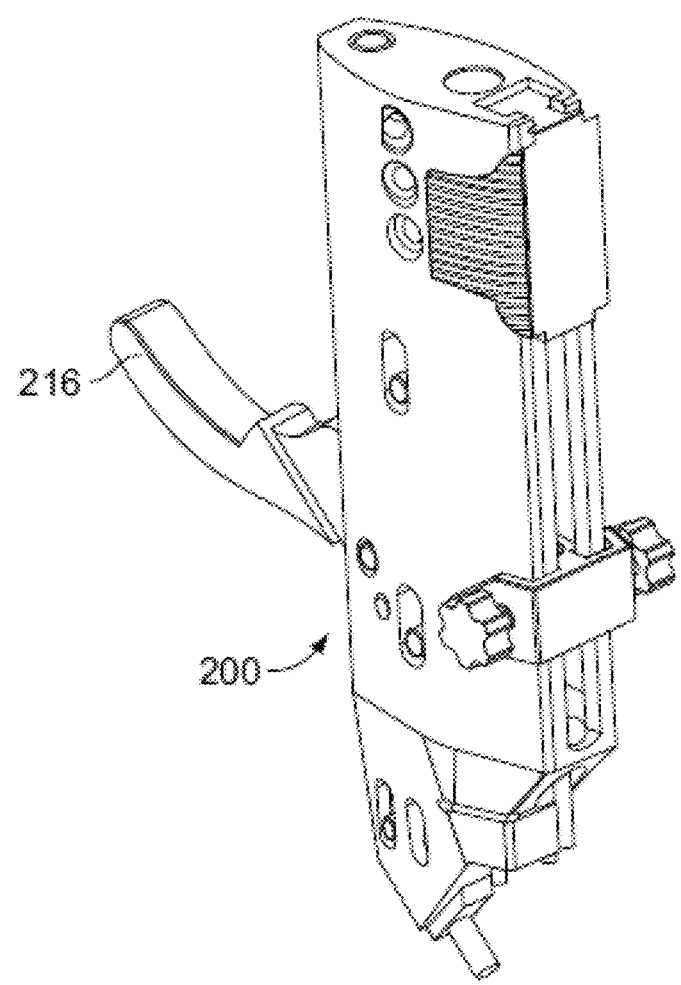
FIG. 4D is a perspective view of the height measuring gauge of FIG. 3 in an unlocked configuration with the pointer in the second position and the slider in the first position.

Before or after causing such expansion, the user may grip slider 240 and slide it distally until a distal end surface 249 of bone position indicator 248 makes contact with a bearing surface 14 of the humerus, the position of slider 240 and pointer 250 being shown in FIG. 4B. At this stage, knobs 256 may be tightened to frictionally engage handle body 212. Pointer 250 may now serve as an objective reference to a height of trial stem 100 with respect to humerus 10 for later reference. Because pointer 250 is frictionally locked, slider 240 may be slid proximally while the pointer remains in place, the magnetic interaction between magnet 258 and the main body 242 of the slider not affecting the position of the pointer, as illustrated in FIG. 4C. Once pointer 250 is locked into the desired position and slider 240 is back at an original proximal position, handle portion 210 may be shifted to the unlocked configuration by actuating loading member 216 as described above. This allows a user to remove height measuring gauge 200, as shown in FIG. 4D, while leaving trial stem 100 expanded in place.

With trial stem 100 secure in place, any one of a number of additional trial components may be attached to trial stem 100 via trial recess 114, such as a trial humeral head or a reverse cup humeral trial (not shown). One benefit of the trial stem 100 illustrated herein is that the trial recess 114 may provide compatibility with a greater number of other trial components compared to known expandable trial stems that have a protruding peg or similar protruding structure onto which other trial components fit. The position of trial recess 114 is possible at least partly due to the location of expandable bolt 130. In certain known expandable trial stems, an expansion bolt extended close to the proximal end of the known trial stem, making such a trial recess incompatible as any component inserted into a recess made in the known trial would make contact with a proximal end of the expansion bolt. However, the relatively distal position of expansion bolt 130 and its total encapsulation within trial stem 100, as disclosed herein, facilitates the ability of using trial recess 114 which, as noted above, may accept a number of different types of trial components. Once the desired trial component is connected to trial stem 100, the user may conduct trialing to confirm the size and placement of trial stem 100 as well as any other trial components being used.

Figure 5A:
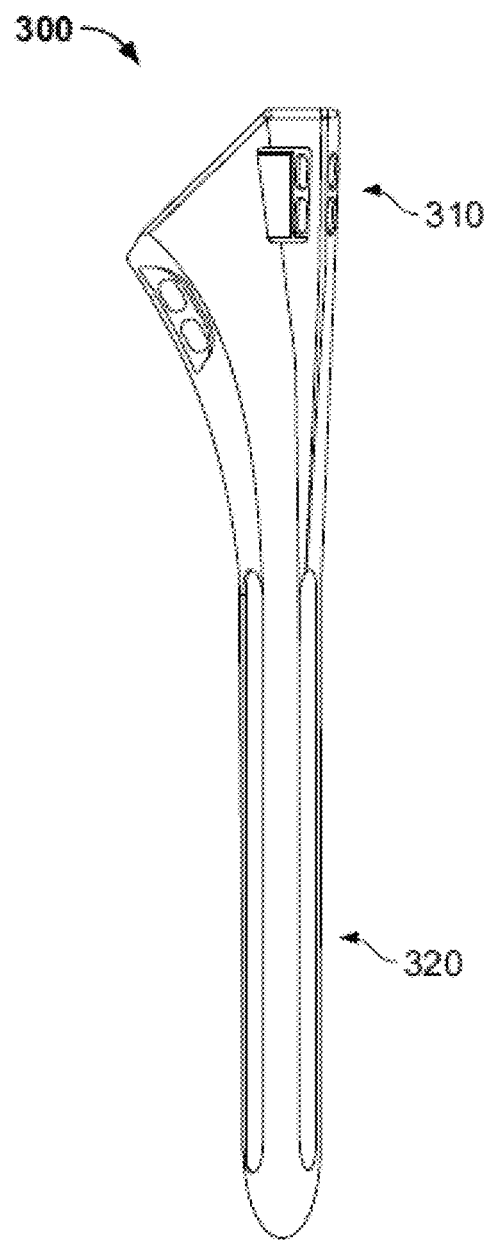
FIG. 5A is a perspective view of one embodiment of a stem implant according to aspects of the disclosure.
Figure 5B:
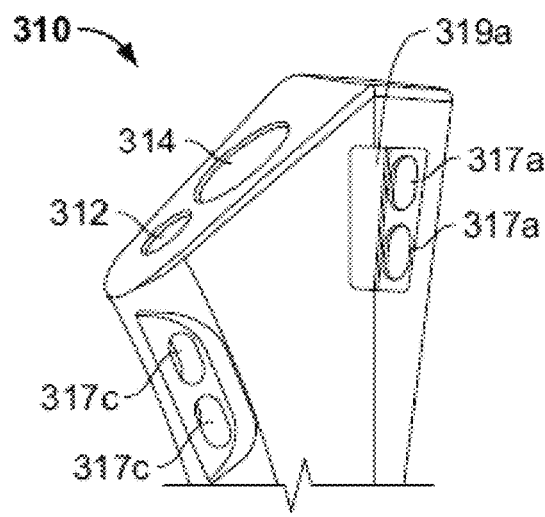
FIG. 5B is a perspective view of a proximal portion of the stem implant of FIG. 5A.
Figure 5C:
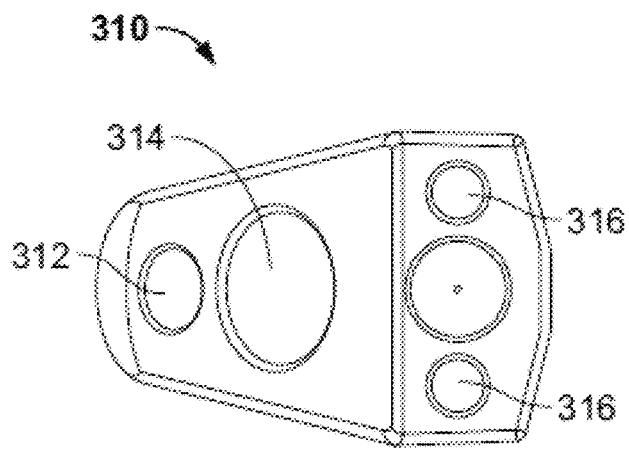
FIG. 5C is a top view of the stem implant of FIG. 5A.
Figure 5D:
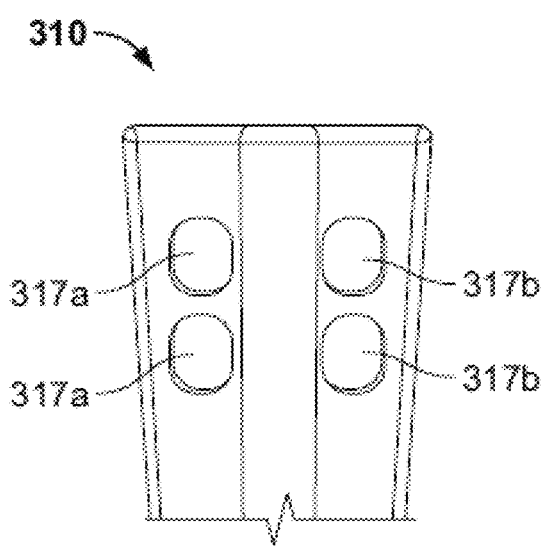
FIG. 5D is a side view of a proximal portion of the stem implant of FIG. 5A.

After the user is satisfied with the results of trialing, any trial components still connected to trial stem 100 may be removed. Trial stem 100 may then be removed, with or without the use of height measuring gauge 200. Based on the results of trialing, a particular sized stem implant 300 is chosen. An exemplary embodiment of stem implant 300 is illustrated in FIG. 5A and may be structurally similar to trial stem 100 in certain respects. Stem implant 300 may be monolithic with a proximal portion 310 and a distal portion 320. Proximal portion 310 of stem implant 300, shown in greater detail in FIGS. 5B-D, may include a catch aperture 312, an implant recess 314, and two locking pin apertures 316. The apertures 312, 316, similar to corresponding features on trial stem 100, facilitate the connection between handle portion 210 of height measuring gauge 200 with stem implant 300. Implant recess 314 may be configured to accept a humeral head implant, reverse cup humeral implant, or other compatible implant. Proximal portion 310 may also include a number of features to facilitate securing portions of humerus 10, such as first segment 20 and second segment 30, to stem implant 300. For example, a first pair of suture holes 317a may be formed on a lateral-anterior side of proximal portion 310 and a second pair of suture holes 317b may be formed on a lateral-posterior side of the proximal portion. A third pair of suture holes 317c may be formed on a medial side of proximal portion 310. The suture holes 317a-c may facilitate securing one or more bone fragments to stem implant 300 via sutures (not illustrated). One suture pocket 319a may be formed on the lateral-anterior side of proximal portion 310, and may be connected to suture holes 317a. Another suture pocket (not visible in FIGS. 5A-D) may be formed on the lateral-posterior side of proximal portion 310, and may be connected to suture holes 317b. The suture pockets may, for example, facilitate the insertion of a suture needle.

Figure 6A:
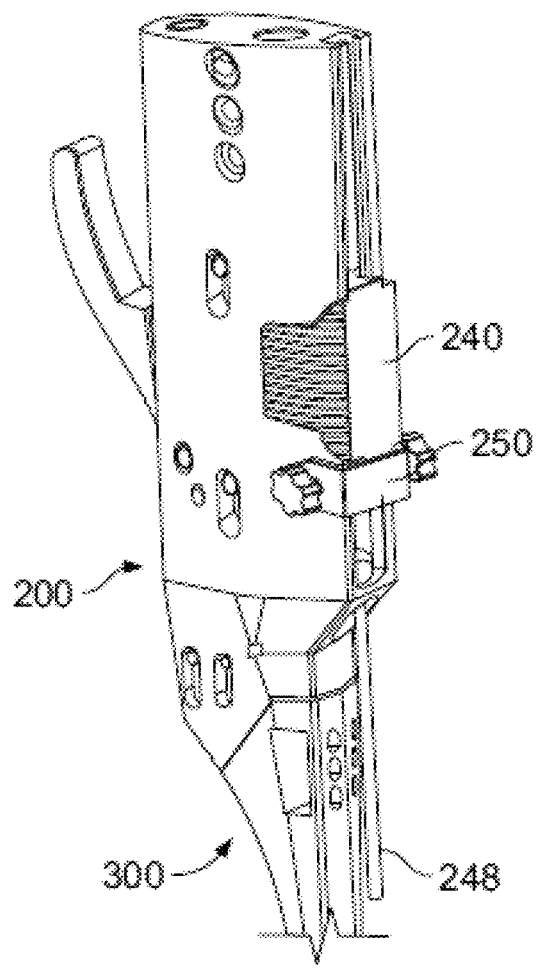
FIG. 6A is a perspective view of the stem implant of FIG. 5A attached to the height measuring gauge of FIG. 3 in a locked configuration with the pointer and slider in a second position.

After the desired stem implant 300 is chosen, the user may connect the stem implant to height measuring gauge 200 and lock the stem implant using loading member 216, as described above. Once locked into place, a user may insert stem implant 300 into the prepared hole in humerus 10 using height measuring gauge 200. At this stage, pointer 250 is still locked into the position determined during insertion of trial stem 100, described above in relation to FIGS. 4A-C. The user may slide slider 240 distally until it contacts pointer 250, as illustrated in FIG. 6A. The user may confirm that the distal end of bone position indicator 248 is in contact with bearing surface 14 of the proximal portion 12 of humerus 10. This confirms that the height of stem implant 300 with respect to humerus 10 corresponds to the desired height determined using trial stem 100, reducing or eliminating the requirement for the user to subjectively assess the respective heights.

The user may assess and confirm a correct rotational position of stem implant 300 at this point using one or more of threaded apertures 260, 270, and 280, as shown in FIG. 4B. Each threaded aperture 260, 270, and 280 is a threaded aperture at varying angles. For example, one of the threaded apertures may be angled at approximately 20 degrees, another may be angled at approximately 30 degrees, and the third may be angled at approximately 40 degrees. A version rod taking the form of a straight rod with a threaded end may be threaded into any one of the threaded apertures 260, 270, or 280. The version rod may be used to provide a line of reference for comparison, for example, with the position of the forearm relative to the shoulder. When the version rod aligns with the desired anatomical landmark(s), the angle will be known or estimated based on which threaded aperture 260, 270, or 280 the version rod extends from. More or fewer than three threaded apertures may be provided, and the particular angles are not limited to 20, 30, and 40 degrees. Further, threaded apertures may be provided on one or both sides of handle 210. This procedure is essentially the same whether measurements are being taken in relation to trial stem 100 or stem implant 300.

Figure 6B:
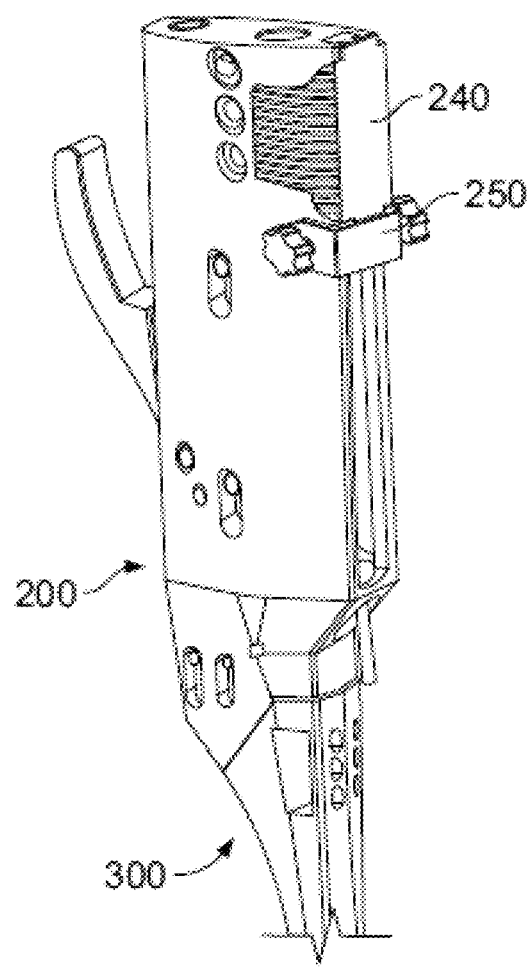
FIG. 6B is a perspective view of the stem implant of FIG. 5A attached to the height measuring gauge of FIG. 3 in a locked configuration with the pointer and slider in a first position.

Once version has been confirmed, the user may then unscrew the knobs 256 of pointer 250, causing the pointer to transition into an unlocked configuration. Then, slider 240 may be slid proximally, causing pointer 250 to slide proximally due to the magnetic connection between the pointer and slider, as illustrated in FIG. 6B. Finally, the user may rotate loading member 246 to unlock handle portion 210 of height measuring gauge 200 from stem implant 300. At this point, the user may attach a humeral head or other implant component to stem implant 300, and complete the particular implant procedure desired.

Figure 7A:
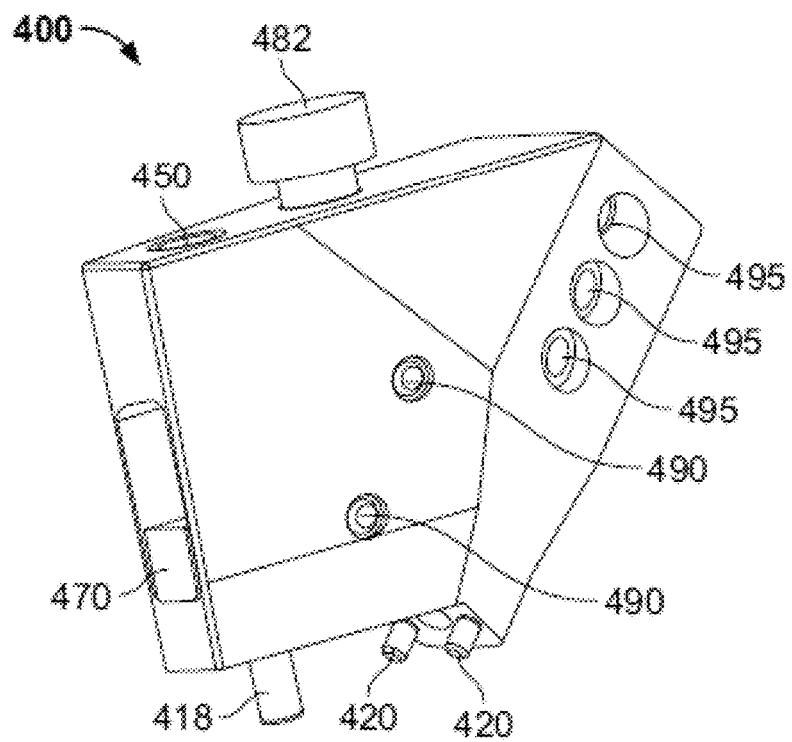
FIG. 7A is a perspective view of one embodiment of a version block according to an aspect of the disclosure.
Figure 7B:
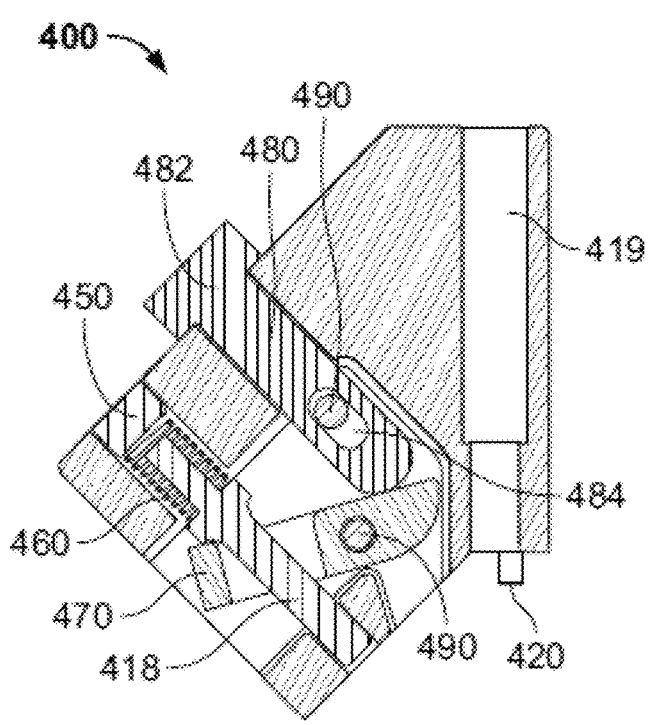
FIG. 7B is a cross-sectional view of the version block of FIG. 7A.

As noted above, during the procedure, it may be desirable to assess and confirm a correct rotational position of trial stem 100 and/or stem implant 300. One method of assessing and/or confirming version was described above in relation to threaded apertures 260, 270, and 280 of handle 210. A version block 400, as illustrated in FIG. 7A, may be used in conjunction with a version rod (not illustrated) to determine the rotational position of stem implant 300 or trial stem 100 if a user does not wish to use threaded apertures 260, 270, and 280 of handle 210. Generally, version block 400 is a monolithic structure with a number of components that facilitate locking of the version block to stem implant 300. In particular, version block 400 may include a pair of locking pins 420 configured to mate with locking pin apertures 316 of stem implant 300. Version block 400 may also include a catch member 418 configured to mate with catch aperture 312 of stem implant 300. As illustrated in FIG. 7B, version block 400 may also include a driver recess 419 configured to allow passage of a driving tool through the version block and into trial stem 100 when the version block is attached to the trial stem.

Figure 7C:
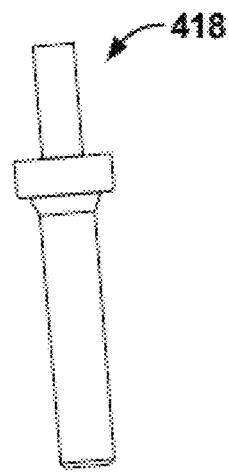
FIG. 7C is an isolated perspective view of a catch member of the version block of FIG. 7A.
Figure 7D:
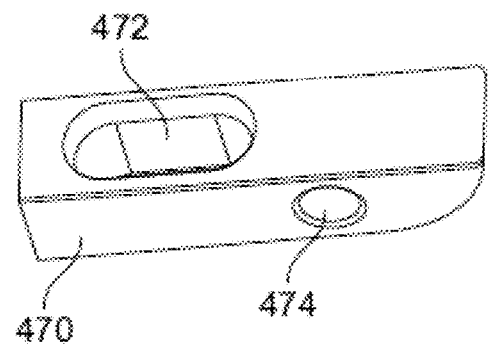
FIG. 7D is an isolated perspective view of a lever of the version block of FIG. 7A.

Still referring to FIG. 7B, the locking mechanism of version block may generally include catch member 418, spring cap 450, spring 460, lever 470, and actuator 480. Catch member 418, which is also illustrated in FIG. 7C, may be a generally cylindrical member with a flange that cooperates with spring 460, the spring contacting the flange of the catch member on a first end and spring cap 450 on a second end opposite the first end. This configuration provides for a force that biases catch member 418 beyond a distal end of version block 400. A distal end of the flange of catch member 418 may be configured to contact a proximal face of lever 470, with a cylindrical portion of the catch member extending through a slot 472 in the lever. Lever 470, which is also illustrated in FIG. 7D, is configured to pivot about pin 490, the pin connecting the lever to version block 400 through a pin aperture 474 in the lever. The flange of catch member 418 does not fit through slot 472 in lever 470, so the biasing force provided by spring 460 on the catch member is transmitted to the lever, causing the lever to be biased in a counterclockwise direction in the view of FIG. 7B. One end of lever 470 is configured to contact a distal end of actuator 480. Actuator 480 may generally comprise a cylindrical pin with an enlarged head 482 and a slot 484. Actuator 480 is connected to version block 400 by another pin 490 extending through slot 484 of the actuator. Actuator 480 may slide into or out of version block 400, the sliding motion being limited by enlarged head 482 and the cooperation of pin 490 with slot 484. As should be understood from the description of the components above, actuator 480 is biased in a proximal direction resulting from the transmission of force from spring 460 to catch member 418 to lever 470 and finally to the actuator. Thus, a user may press distally on the enlarged head 482 of actuator 480 to cause catch member 418 to retract within the body of version block 400. Similarly, a user may stop the application of force on the enlarged head 482 of actuator 480 to cause the spring 460 to push catch member 418 partially out of version block 400.

Figure 7E:
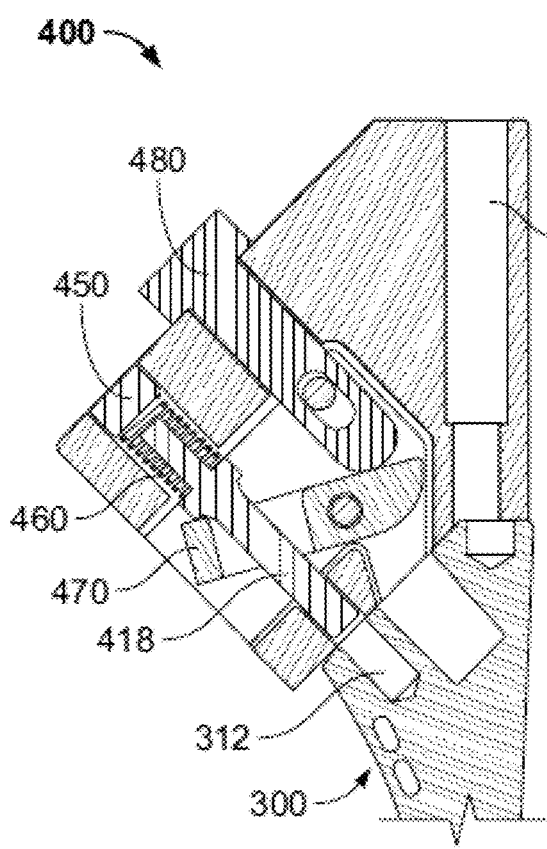
FIG. 7E is a cross-sectional view of the version block of FIG. 7A attached to the stem implant of FIG. 5A in an unlocked configuration.
Figure 7F:
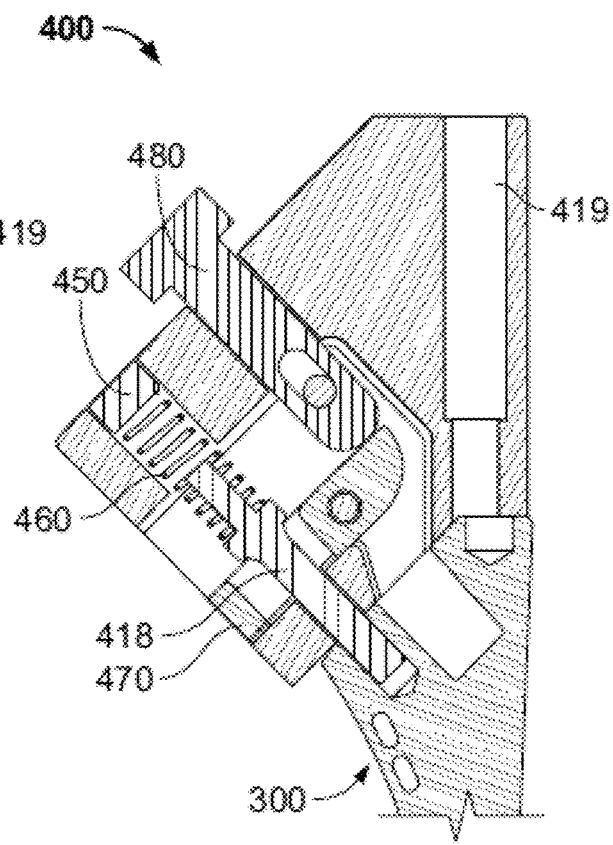
FIG. 7F is a cross-sectional view of the version block of FIG. 7A attached to the stem implant of FIG. 5A in a locked configuration.

To lock version block 400 to stem implant 300, a user depresses actuator 480 to retract catch member 418 inside the version block. Locking pins 420 are inserted into corresponding locking pin apertures 316 of stem implant 300, as illustrated in FIG. 7E. The user then aligns catch member 418 with catch aperture 312 and releases actuator 480, causing the bias force provided by spring 460 to push the catch member distally out of version block 400 and into corresponding catch aperture 312 of stem implant 300, as illustrated in FIG. 7F. Once in the locked configuration, a version rod (not illustrated) may be inserted into any one of a number of version rod apertures 495 in version block 400, as illustrated in FIG. 7A. The version rod may be generally "L" shaped or straight, as noted above, with one end of the rod extending to provide a line of reference for comparison, for example, with the position of the forearm relative to the shoulder. As noted above, version block 400 may be used with trial stem 100 or stem implant 300 to assess the rotational position of the trial stem or stem implant in relation to the anatomy during trialing or assessment of implant position. Because version rods are generally known in the art, they are not described in greater detail herein.

Figures 8A, 8B:
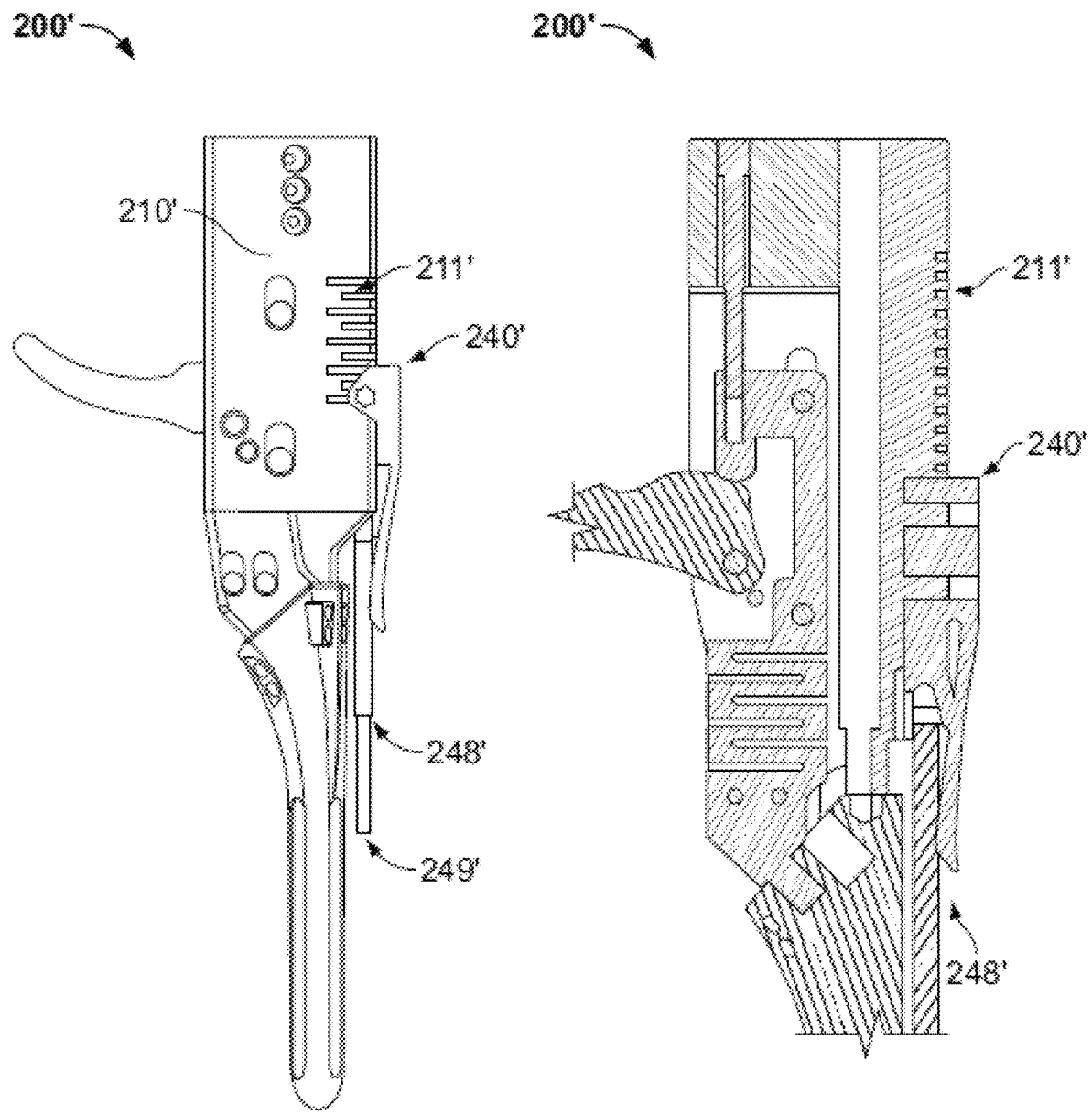
FIG. 8A is a side view of a height measurement gauge according to another aspect of the disclosure.
FIG. 8B is a cross-sectional view of the height measurement gauge of FIG. 8A.

An alternate embodiment of height measurement gauge 200' is illustrated in FIGS. 8A-8B. Height measurement gauge 200' is similar to height measurement gauge 200 in nearly all respects, with the exception of the following. The height measurement system only includes a sliding member 240', without a pointer as provided with height measurement gauge 200. Sliding member 240' may include a marking, such as an arrow or a notch, to reference corresponding indicia 211' on the handle body 210' of height measurement gauge 200'. During insertion of trial stem 100, slider 240' is slid distally until a distal end surface 249' of bone position indicator 248' makes contact with a bearing surface 14 of the humerus, much in the same way as described in connection with height measurement gauge 200. In this embodiment, the user may take note of the position of the arrow or other indicator on sliding member 240' with respect to indicia 211' on the body of handle 210'. This provides an objective indication of the position of bone position indicator 248' when trial stem 100 is properly inserted into the bone. When inserting stem implant 300 using height measurement gauge 200', sliding member 240' may be positioned so that the arrow or other indicator aligns with the corresponding indicia 211' as determined while using trial stem 100. In addition, sliding member 240' may include teeth, screws, or other members to lock the sliding member 240' in a particular position with respect to the body of handle 210'. For example, a structure similar to knobs 256 of pointer 250 may be used with sliding member 240' to achieve such locking.

Figure 9A:
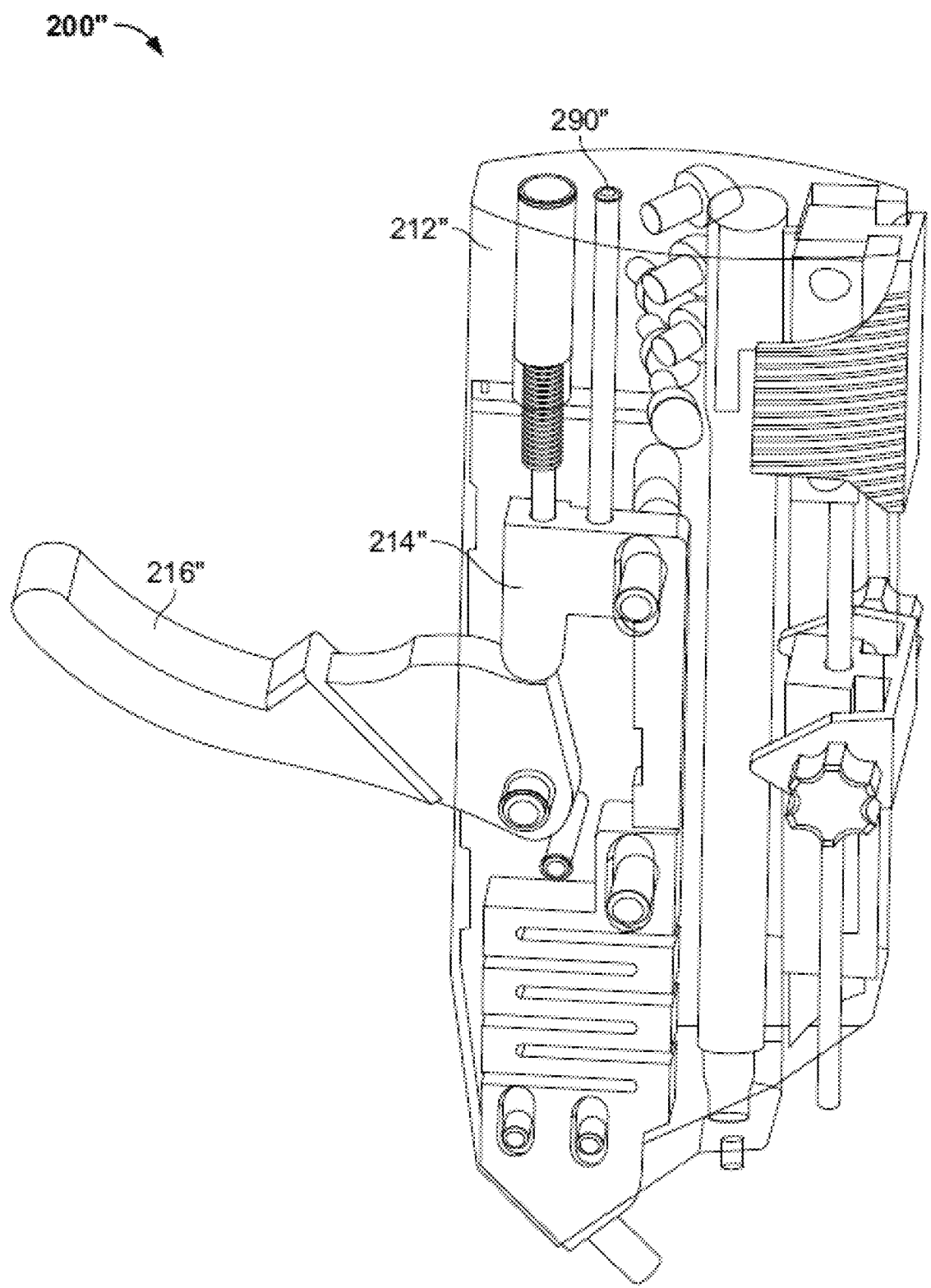
FIG. 9A is a perspective view of a height measuring gauge according to another aspect of the disclosure in partial transparency in an unlocked configuration.
Figures 9B, 9C:
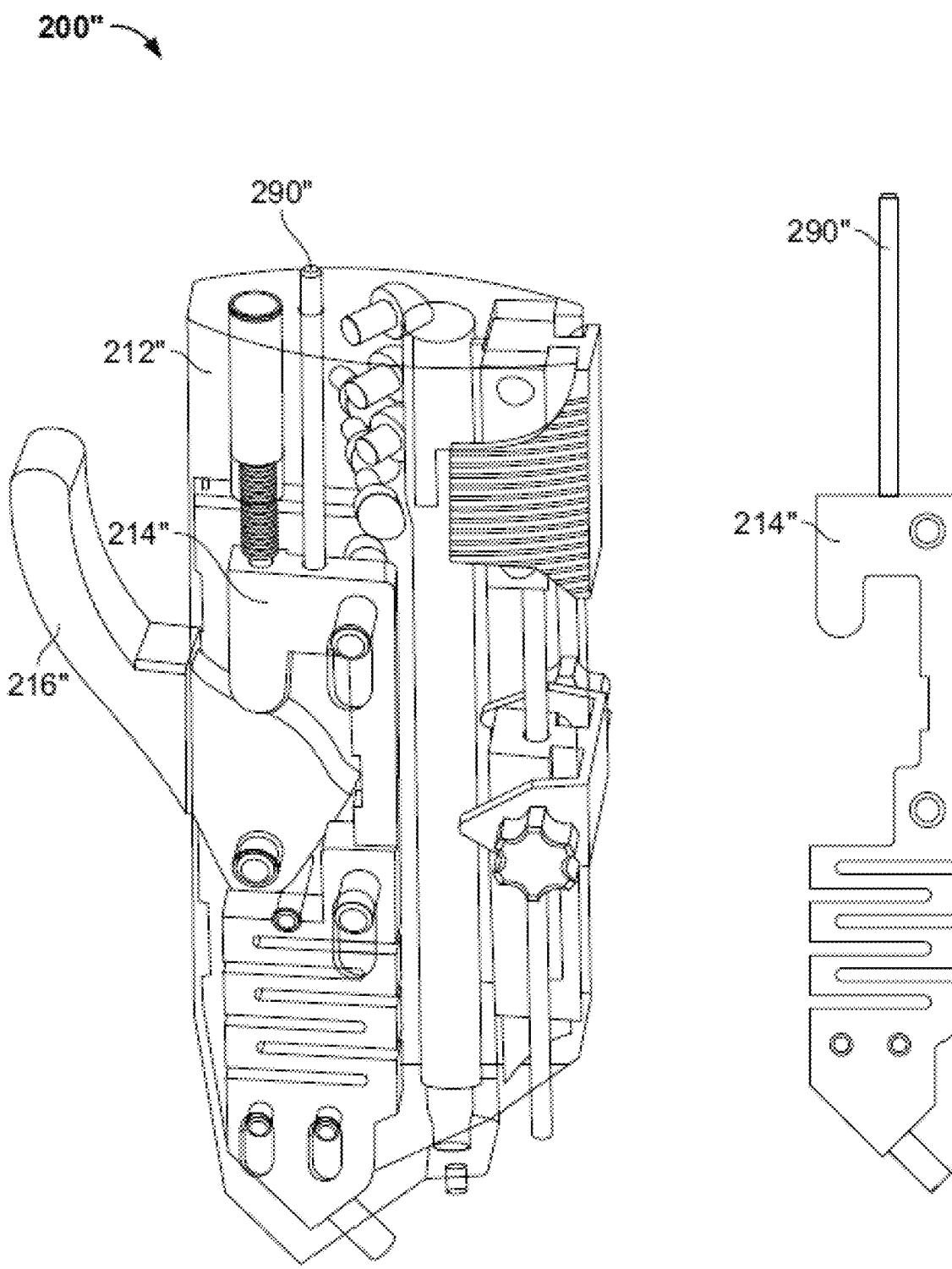
FIG. 9B is a perspective view of the height measurement gauge of FIG. 9A in partial transparency in a locked configuration.
FIG. 9C is a side view of a deformable plate and locking status indicator of the height measurement gauge of FIG. 9A.

Another embodiment of height measuring gauge 200" is illustrated in FIGS. 9A-B. Height measuring gauge 200" is nearly identical to height measuring gauge 200, with the exception that height measuring gauge 200" includes a locking status indicator mechanism, for example locking status pin 290". Pin 290" extends from a proximal portion of deformable plate 214" and is positioned within a corresponding cavity defined by handle body 212". Pin 290" may be welded or otherwise fixed to deformable plate 214" but free to slide within the corresponding cavity defined by handle body 212". Pin 290" may help indicate to the user whether loading member 216" is in a locked or unlocked configuration. For example, when in an unlocked configuration, as shown in FIG. 9B, pin 290" may be generally flush with a proximal end of handle body 212". After a transition to a locked configuration, as shown in FIG. 9B, pin 290" may be pushed proximally so as to extend beyond the proximal end of handle body 212", providing a user with a visual indication that loading member 216" is in a locked configuration. The length and position of pin 290" may be altered to vary the exact position of the pin that indicates the locked or unlocked configuration. Deformable plate 214" and pin 290" are illustrated without handle body 212" in FIG. 9C.

Figure 10A:
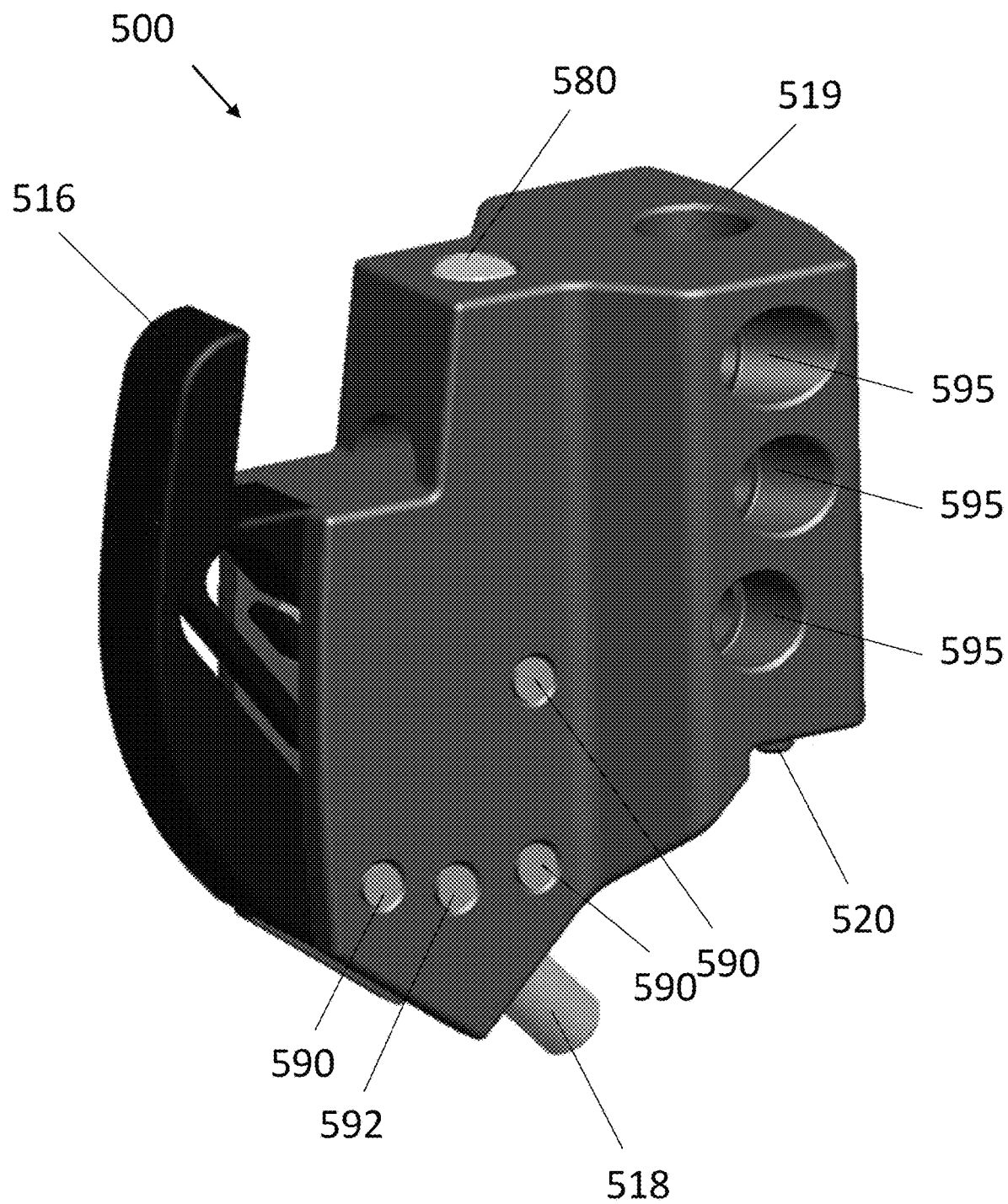
FIG. 10A is a perspective vies of a version block according to another aspect of the disclosure.

FIG. 10A is a perspective view of a version block 500 that combines aspects of the various handles and version blocks described above. Version block 500 may be a monolithic structure with a number of components that facilitate locking of the version block to trial stem 100 and/or stem implant 300. In particular, version block 500 may include a pair of locking pins 520 (only one visible in FIG. 10A) configured to mate with the locking pin apertures of trial stem 100 and locking pin apertures 316 of stem implant 300. Version block 500 may also include a catch member 518 configured to mate with catch aperture 112 of trial stem 100 and catch aperture 312 of stem implant 300. The catch member 518 and locking pins 520 may extend from the distal end of the version block 500 at non-parallel angles. Version block 500 may include a driver recess 519 configured to allow passage of a driving tool through the version block and into trial stem 100 when the version block is attached to the trial stem.

Figure 10B:
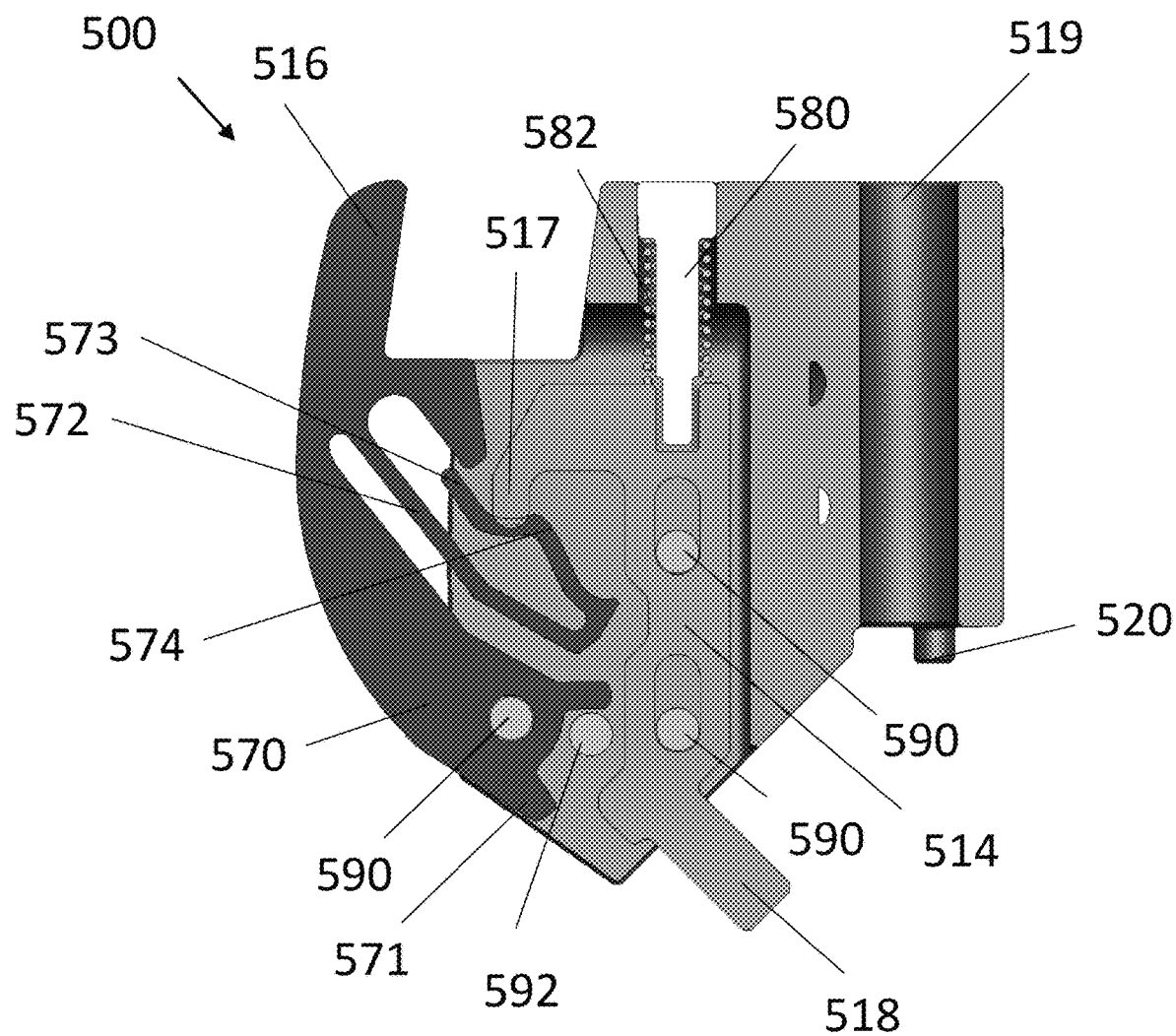
FIG. 10B is a cross-section of the version block of FIG. 10A in a locked condition, with a corresponding implant omitted from the view.
Figure 10C:
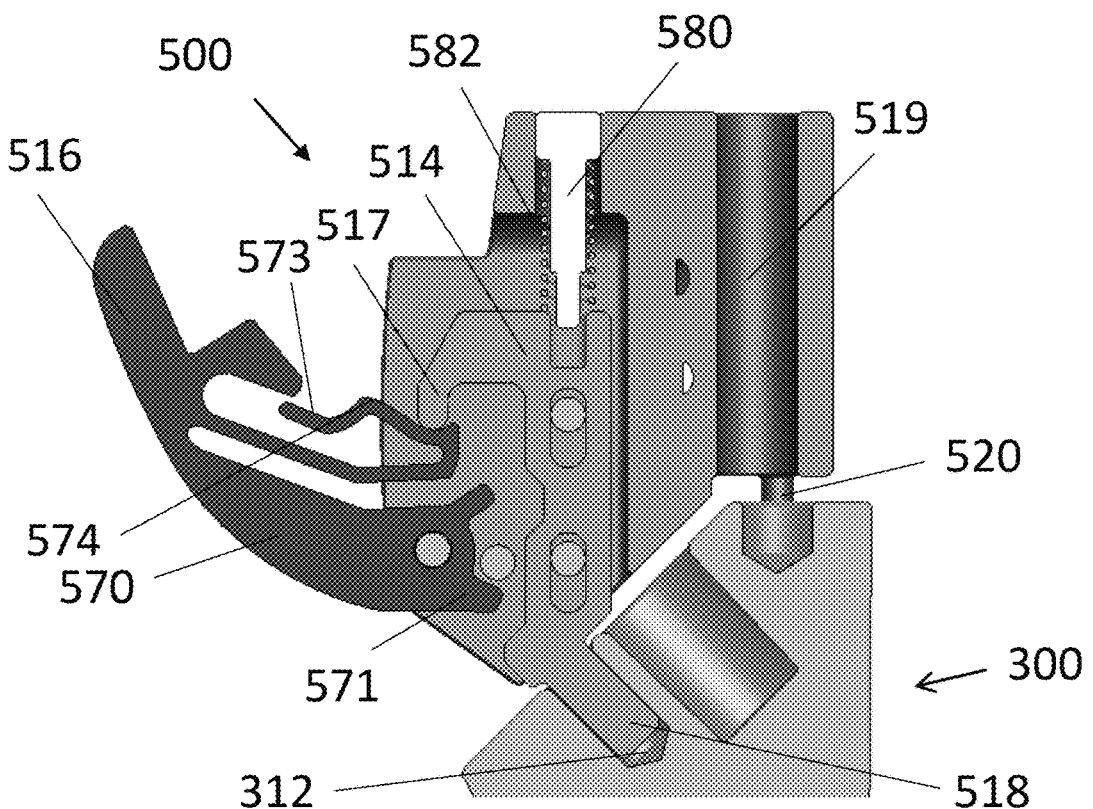
FIG. 10C is a cross-section of the version block of FIG. 10A coupled to the stem implant of FIG. 5A in an unlocked condition.

FIG. 10B illustrates a cross-section of version block 500. The locking mechanism of version block 500 may generally include a loading member 516, which may be a rotatable handle, and a plate 514 which includes catch member 518. Catch member 518 may be a generally cylindrical member coupled to a distal end of plate 514. An actuator 580 may include a distal tip that may fit within a recess in the proximal end of plate 514. Actuator 580 may be a pin and include a proximal cap that is fixed with respect to the housing of version block 500, with a spring 582 positioned around actuator 580, with a proximal end of the spring abutting the proximal cap of the actuator. A distal end of spring 582 may abut a proximal end of plate 514. Plate 514 may include one or more vertical slots that engage with pins 590, so that the plate is able to move vertically with the slots sliding over the pins. With this configuration, spring 582 biases plate 514 to a distal position relative to the version block 500 in the absence of applied forces. This position may be referred to as an unlocked condition and is shown in FIG. 10C. Plate 514 may include a hooked projection 517 that interacts with loading member 516 to assist in transitioning the version block from an unlocked condition, shown in FIG. 10C, through an intermediate condition shown in FIG. 10D, to a locked condition, shown in FIGS. 10E-F, as described in greater detail below.

Referring to FIG. 10C, while version block 500 is in the unlocked condition, catch member 518 may be inserted into the catch member aperture 312 of the stem implant 300 (or the corresponding catch member of the trial stem 100) and locking pins 520 may be inserted into the locking pin apertures 316 of the stem implant (or the corresponding locking pin apertures of the trial stem). Loading member 516 includes a body 570 with an aperture that a pin 590 may pass through so that the loading member is rotatable about the pin. Body 570 may include a pair of projections 571 that are positioned on either side of a stopper pin 592, which may be similar or identical in structure to the other pins 590. The projections 571 may limit the range which the loading member 516 may rotate, with the projections contacting the stopper pin 592 at the maximum ranges of rotation in either direction. Loading member 516 may also include a flexure member 572 that has a first end coupled to loading member 516 and a second free end 573. Flexure member 572 may be generally "U"-shaped so that the flexure member extends in a first direction from its connection point to loading member 516, and then turns back so that the second free end 573 is substantially parallel to the first end of the flexure member. With this configuration, the second free end 573 may move toward (or away from) the first end of flexure member 572 as compressive force is applied to (or released from) the second free end 573.

Figure 10D:
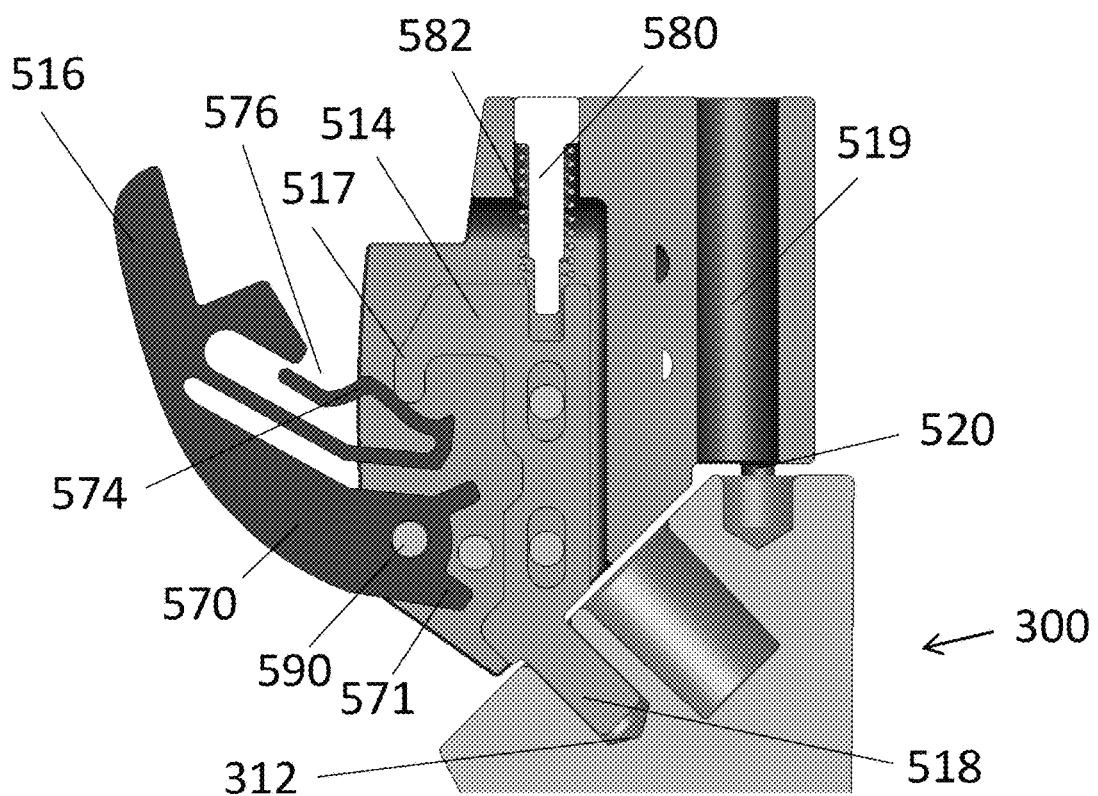
FIG. 10D is a cross-section of the version block of FIG. 10A coupled to the stem implant of FIG. 5A in an intermediate condition.
Figure 10E:
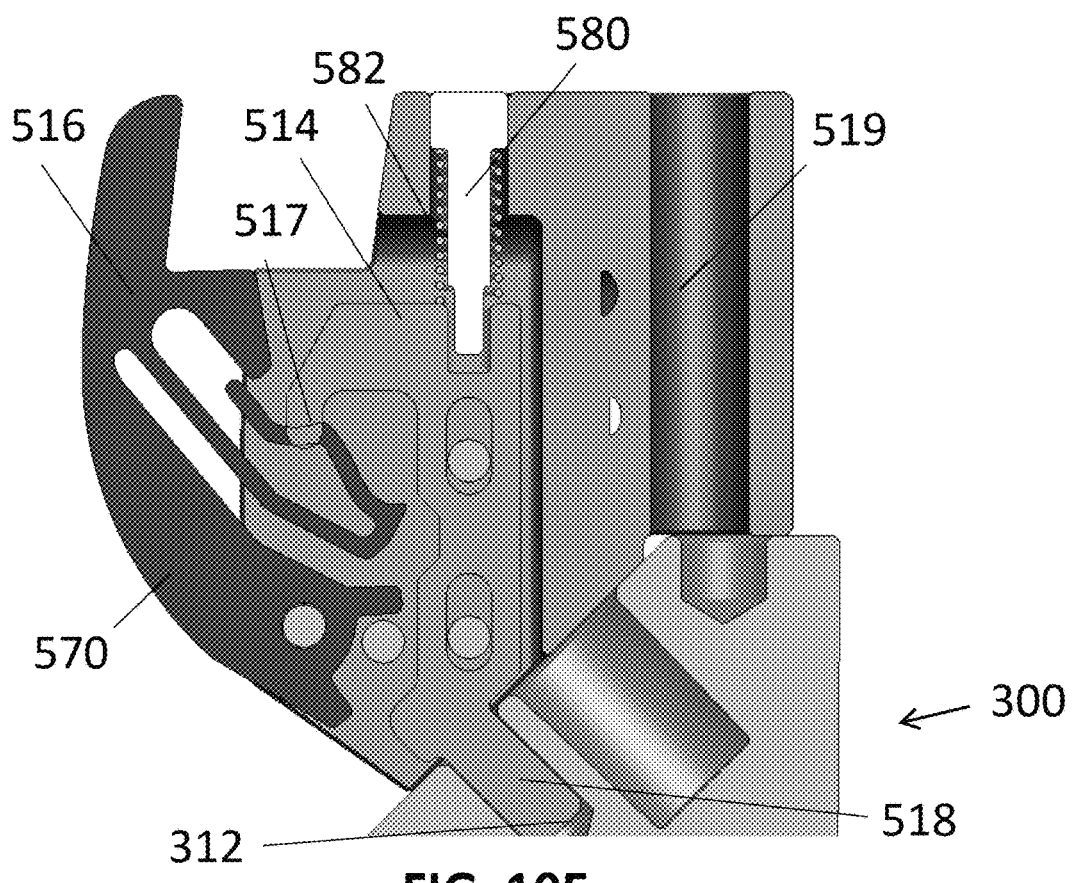
FIG. 10E is a cross section of the version block of FIG. 10A coupled to the stem implant of FIG. 5A in a locked condition.
Figure 10F:
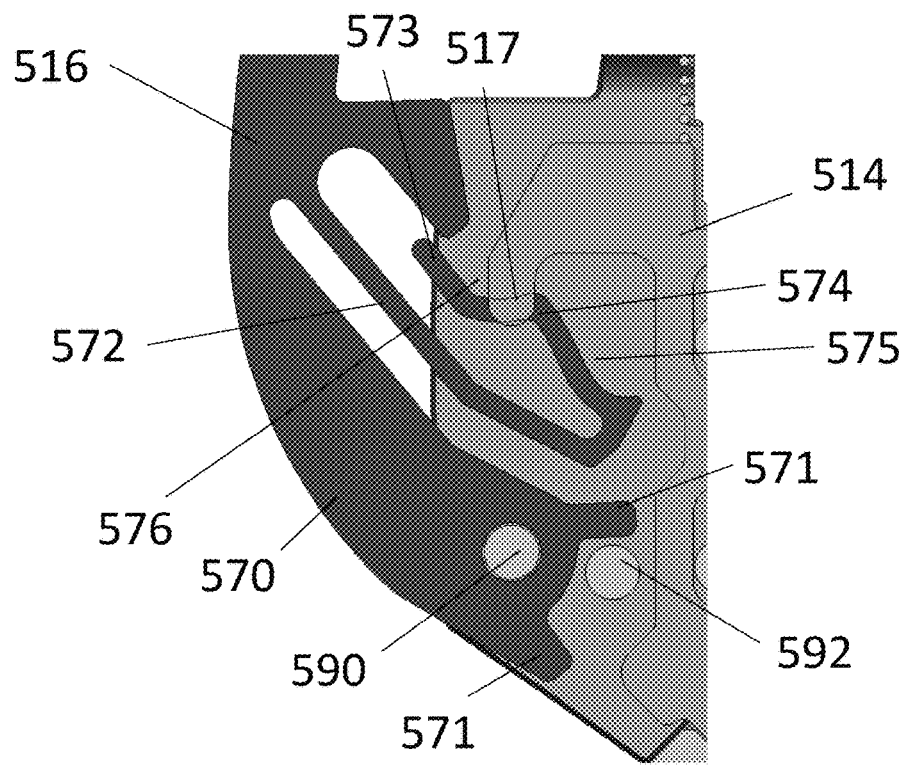
FIG. 10F is an enlarged cross section of the version block shown in FIG. 10E.

The second end 573 of flexure member 572 may include a projection 574, with grooves 575, 576 on either side of the projection. In the unlocked condition of version block 500, shown in FIG. 10C, the projection 517 of plate 514 may rest within groove 575. One of the projections 571 of body 570 of loading member 516 may help ensure that the flexure member 572 cannot be rotated so that the projection 517 loses contact with the flexure member. With the catch member 518 within the catch aperture 312 of implant stem 300 (or otherwise within the corresponding catch aperture of the trial stem 100), the user may begin to rotate loading member 516 clockwise in the view of FIG. 10C. As the loading member 516 is rotated clockwise about pin 590, the projection 517 of plate 514 begins to ride up the second end 573 of flexure member 572 toward projection 574, as shown in FIG. 10D. In the intermediate condition of version block 500, shown in FIG. 10D, the flexure member 572 begins to compress as the second end 573 of the flexure member moves toward the first end. As the projection 517 rides up the flexure member 572 toward projection 574, plate 514 is pulled proximally causing spring 582 to compress. The user may continue to rotate loading member 516 until projection 517 passes over projection 574 and comes to rest in groove 576 and the version block 500 is in the locked condition shown in FIG. 10E. Once the projection 517 passes over projection 574, the flexure member 572 springs back to relieve some of the compressive forces previously applied on the flexure member. In the locked condition, the catch member 518 is pulled proximally in catch aperture 312 of stem implant 300 (or the corresponding catch aperture in trial stem 100). Similar to the other embodiments described herein, the force applied to catch member 518 combined with the positioning of locking pins 520 within corresponding locking pin apertures 316 of stem implant 300 or corresponding locking pin apertures of trial stem 100, results in the version block 500 being locked to the stem implant or trial stem. Once the version block 500 is in the locked condition of FIGS. 10E-F, the user may release the loading member 516. The projection 574 of flexure member 572 maintains the projection 517 of plate 514 in groove 576 in the absence of applied force. Further, the flexure member 572, in the locked condition of the version block 500, applies an upward force on plate 514 so that version block 500 maintains a compressive force on the stem implant 300 or trial stem 100. The second projection 571 of the main body 570 may interact with stopper pin 592 to limit further rotation of the loading member 516 in the clockwise direction.

When version block 500 is in the locked condition, the trial stem 100 may be inserted into the proximal humerus 12 and then expanded by passing a driver tool through the driver recess 519 and expanding the trial as described in connection with other embodiments above. The height of the trial stem 100 may be determined, for example by using indicia or other markings on the trial stem that correspond to height indicia or markings on stem implant 300. Version may be confirmed by using a version rod with one or more version rod apertures 595, in substantially the same manner as described in connection to version block 400. If the trialing is successful, the user may de-expand the trial stem 100 and remove trial stem 100 from the humerus 12 by pulling the version block 500 proximally. The version block 500 may be transitioned to the unlocked condition and decoupled from the trial stem 100. While in the unlocked condition, version block 500 coupled to stem implant 300, and transitioned back to the locked condition. The stem implant 300 may then be inserted into the proximal humerus 12 until the height markings or indicia on the stem implant are at the height previously recorded from the trial stem 100. Version may again be confirmed using a version rod (not shown) with version rod apertures 595, in substantially the same manner as described in connection with other embodiments above. If the implant position is satisfactory, the user may transition the version block 500 to the unlocked condition and remove the version block from the stem implant 300, leaving the stem implant in place. Additional components, such as a prosthetic humeral head, may be coupled to the stem implant 300 and the procedure completed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic shoulder implant system comprising:
a prosthetic humeral implant including a catch member aperture and a first locking pin aperture; and
a version device for measuring a rotational position of the prosthetic humeral implant including:
a body portion;
a rotatable member having a handle and a flexure member, the rotatable member rotatably coupled to the body portion of the version device;
a plate having a catch member adapted to mate with the catch member aperture, and a projection in contact with the flexure member, the catch member extending from a distal portion of the body portion of the version device along a first axis, the plate being translatable relative to the body portion of the version device; and
a first locking pin extending from the distal portion of body portion of the version device along a second axis non-parallel to the first axis and adapted to mate with the first locking pin aperture;
wherein in an unlocked condition of the system, the rotatable member has a first rotated position in which the flexure member is in an uncompressed state and the plate is in a first position, and in a locked condition of the system, the rotatable member has a second rotated position in which the flexure member is moveable relative to the handle and is in a compressed state and the plate is in a second position proximal of the first position.

2. The system of claim 1, wherein the prosthetic humeral implant is a permanent implant stem.

3. The system of claim 2, wherein the permanent implant stem includes a plurality of indicia for marking the height of the permanent implant stem.

4. The system of claim 1, wherein the prosthetic humeral implant is a trial stem implant.

5. The system of claim 4, wherein the trial stem implant includes a plurality of indicia for marking the height of the trial stem implant.

6. The system of claim 1, further comprising a biasing member biasing the plate to the first position.

7. The system of claim 1, wherein the handle of the rotatable member includes a first projection in contact with a stopper pin when the rotatable member is in the first rotated position, the first projection resisting rotation of the rotatable member in a first rotational direction.

8. The system of claim 7, wherein the handle of the rotatable member includes a second projection in contact with the stopper pin when the rotatable member is in the second rotated position, the second projection resisting rotation of the rotatable member in a second rotational direction opposite the first rotational direction.

9. The system of claim 1, wherein the flexure member includes a first groove, a second groove, and a projecting portion between the first and second grooves.

10. The system of claim 9, wherein in the unlocked condition of the system, the projection of the plate is positioned within the first groove.

11. The system of claim 10, wherein in the locked condition of the system, the projection of the plate is positioned within the second groove.

12. The system of claim 11, wherein the system includes an intermediate condition in which the rotatable member is in a third rotated position between the first and second rotated positions and the projection of the plate contacts the projecting portion of the flexure member.

13. The system of claim 12, wherein the flexure member is at a maximum amount of compression in the intermediate condition of the system.

14. The system of claim 1, wherein when the catch member is positioned within the catch member aperture, the first locking pin is positioned within the first locking pin aperture, and the system is in the locked condition, a compressive force is maintained between the version device and the prosthetic humeral implant.

15. The system of claim 1, wherein the version device includes a plurality of version rod apertures.

16. The system of claim 15, wherein the version rod apertures are threaded apertures configured to mate with a version rod.

17. The system of claim 15, wherein each of the plurality of version rod apertures are angled differently than each other version rod aperture.

18. The system of claim 1, wherein the plate includes a first slot and the version device includes a first plate pin positioned within the first slot.

19. The system of claim 18, wherein the first plate pin guides movement of the plate between the first position of the plate and the second position of the plate.

20. The system of claim 1, wherein the prosthetic humeral implant is a permanent implant stem, and the system further includes a trial stem including a trial catch member aperture adapted to mate with the catch member, and a trial first locking pin aperture adapted to mate with the first locking pin aperture, the permanent implant stem including a plurality of height indicia corresponding to a plurality of height indicia of the trial stem.

* * * * *